US010335426B2

(12) United States Patent
Huizing et al.

(10) Patent No.: US 10,335,426 B2
(45) Date of Patent: *Jul. 2, 2019

(54) N-ACETYL MANNOSAMMINE AS A THERAPEUTIC AGENT

(71) Applicant: The United States of America, as represented by the Secretary, Department of Health and Human Services, Washington, DC (US)

(72) Inventors: Marjan Huizing, Santa Cruz, CA (US); William A. Gahl, Kensington, MD (US); Irini Manoli, Rockville, MD (US); Enriko Klootwijk, London (GB)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/702,529

(22) Filed: Sep. 12, 2017

(65) Prior Publication Data

US 2018/0117072 A1 May 3, 2018

Related U.S. Application Data

(63) Continuation of application No. 14/754,304, filed on Jun. 29, 2015, now abandoned, which is a continuation of application No. 13/791,576, filed on Mar. 8, 2013, now Pat. No. 9,095,597, which is a continuation of application No. 12/530,433, filed as application No. PCT/US2008/006895 on May 30, 2008, now Pat. No. 8,410,063.

(60) Provisional application No. 60/932,451, filed on May 31, 2007.

(51) Int. Cl.
*A61K 31/7008* (2006.01)
*A61K 31/7012* (2006.01)

(52) U.S. Cl.
CPC ...... *A61K 31/7008* (2013.01); *A61K 31/7012* (2013.01)

(58) Field of Classification Search
CPC ... A61K 31/7008; A61K 31/7012; C07H 5/06
See application file for complete search history.

(56) References Cited

U.S. PATENT DOCUMENTS

| | | | |
|---|---|---|---|
| 4,610,868 A | 9/1986 | Fountain et al. | |
| 6,083,935 A | 7/2000 | Wu et al. | |
| 9,341,619 B2 | 5/2016 | Huizing et al. | |
| 2010/0144653 A1 | 6/2010 | Yarema et al. | |
| 2011/0301103 A1 | 12/2011 | Chugh | |

FOREIGN PATENT DOCUMENTS

| | | |
|---|---|---|
| WO | WO 2000/007602 | 2/2000 |
| WO | WO 02/078445 | 10/2002 |
| WO | WO 03/028709 | 4/2003 |
| WO | WO 2004/068970 | 8/2004 |
| WO | WO 2010/131712 | 11/2010 |

OTHER PUBLICATIONS

Agarwal, et al., "Combined peritoneal dialysis . . . " *Perit. Dial. Int.*, 23: 157-161 (2003).
Crook et al., "Relationship between plasma sialic acid . . . " *Diabetes Care* 24(2): 316-322, 2001.
Hong et al., "Lec3 Chinese hamster ovary mutants lack UDP-N-acetylglucosamine 2-epimerase activity because of mutations in the epimerase domain of the Gne gene," *Journal of Biological Chemistry* 278(52): 53045-53054, 2003.
Huizing et al., "N-acetylmannosamine treatment rescues a mouse model of hereditary inclusion body myopathy," *Glycobiology* 16(11): 1110-1111, 2006.
International Search Report from PCT/US2008/006895 dated Oct. 13, 2009.
Kayser et al., "Biosynthesis of a Nonphysiological Sialic Acid in Different Rat Organs, Using N-Propanoyl-D-hexosamines as Precursors," *The Journal of Biological Chemistry*, 267(24): 16934-16938 (Aug. 1992).
Malicdan et al., "A Gne knockout mouse expressing human V572L mutation develops features similar to distal myopathy with rimmed vacuoles or hereditary inclusion body myopathy," *Human Molecular Genetics* 16(2): 115-128, 2007.
Noguchi et al., "Reduction of UDP-N-acetylglucosamine 2-epimerase/ N-acetylmannosamine kinase activity and sialylation in distal myopathy with rimmed vacuoles," *Journal of Biological Chemistry* 279(12): 11402-11407, 2004.
Sparks et al., "Intravenous immune globulin hereditary inclusion body myopathy: a pilot study," *BMC Neurology* 7(1): 3, 2007.
Vasconcelos et al., "Decreased UDP-GTcNAc 2-epimerase/ ManNAc kinase activity in the myotubes of patients with hereditary IBM (HIBM) and GNE mutations: In vitro correction with ManNAc or with free sialic acid and implications for therapy," *Neurology* 60(5) (Supplement 1): A316, 2003.
Written Opinion of the International Search Report from PCT/ US2008/006895 dated Oct. 13, 2009.
Farell et al., "Modulation of Proliferating Renal Epithelial Cell Affinity for Calcium Oxalate Monohydrate Crystals," *J. Am. Soc. Nephrol.*, 175(15): 1748-1750, May 2006.
Galeano et al., "Mutation in the key enzyme of sialic acid biosynthesis causes severe glomerular proteinuria and is rescued by N-acetylmannosamine," *The Journal of Clinical Investigation*, 117(6): 1585-1595, Jun. 2007.

(Continued)

*Primary Examiner* — Leigh C Maier
(74) *Attorney, Agent, or Firm* — Klarquist Sparkman, LLP

(57) ABSTRACT

The invention relates to compositions and methods for treating kidney and muscle dysfunction that involves use of therapeutic amounts of N-acetyl mannosamine.

9 Claims, 10 Drawing Sheets
Specification includes a Sequence Listing.

(56) References Cited

OTHER PUBLICATIONS

Extended European Search Report issued for EPC application No. 16196935.7 by the European Patent Office dated Apr. 19, 2017.
Gao et al., "59-AMP-activated protein kinase attenuates Adriamycin-induced oxidative podocyte injury through thioredoxin-mediated suppression of the apoptosis signal-regulating kinase 1—P38 signaling pathway," *Mol. Pharmacol.* (85) 460-471 (Mar. 2014).
Jha et al., "A causal link between oxidative stress and inflammation in cardiovascular and renal complications of diabetes," *Clin. Sci.* 132: 1811-1836 (2018).
Kakani et al., "The Gne M712T mouse as a model for human glomerulopathy," *J. Pathol.* 180(4): 1431-1440 (Apr. 2012).
Leoyklang et al., "Sialylation of Thomsen—Friedenreich antigen is a noninvasive blood-based biomarker for GNE myopathy," *Biomarkers in Medicine* 8(5): 641-652 (2014).
Tanigaki et al., "Hyposialylated IgG activates endothelial IgG receptor FcγRIIB to promote obesity-induced insulin resistance," *Journal of Clinical Investigation* 128(1): 309-322 (Jan. 2018).
Niethamer et al., "Oral monosaccharide therapies to reverse renal and muscle hyposialylation in a mouse model of GNE myopathy," *Molecular Genetics and Metabolism* 107(4):748-55 (Dec. 2012).

N-ACETYL MANNOSAMMINE AS A THERAPEUTIC AGENT

CROSS REFERENCE TO RELATED APPLICATIONS

This application is a continuation of U.S. patent application Ser. No. 14/754,304, filed Jun. 29, 2015, now abandoned, which is a continuation of U.S. patent application Ser. No. 13/791,576, filed Mar. 8, 2013, and issued as U.S. Pat. No. 9,085,597 on Aug. 4, 2015, which is a continuation of U.S. patent application Ser. No. 12/530,433, filed Mar. 19, 2010, and issued as U.S. Pat. No. 8,410,063 on Apr. 2, 2013, which is the U.S. National Stage of International Application No. PCT/US2008/006895, filed May 30, 2008, which was published in English under PCT Article 21(2), which in turn claims the benefit of U.S. Provisional Patent Application No. 60/932,451, filed May 31, 2007, all of which are hereby incorporated by reference.

STATEMENT OF GOVERNMENT SUPPORT

This invention was made with government support under grant no. ZIA HG000215 and grant no. ZIA HG200322 awarded by the National Institutes of Health, National Human Genome Research Institute; the government has certain rights in the invention.

The invention described herein was developed with support from the National Human Genome Research Institute (NHGRI), which is part of the National Institutes of Health (NIH). The United States Government has certain rights in the invention.

FIELD OF THE INVENTION

The invention is related to a methods and compositions involving use of the neutral sugar N-acetyl mannosamine (ManNAc) for therapeutic purposes in humans. Such therapeutic uses include treatment of myopathies (e.g., hereditary inclusion body myopathy (HIBM)) and certain kidney diseases (e.g., those involving proteinuria and hematuria).

BACKGROUND OF THE INVENTION

Hereditary inclusion body myopathy (HIBM; OMIM 600737) is a rare autosomal recessive neuromuscular disorder. Argov, et al., *Neurology* 60, 1519-1523 (2003); Eisenberg, et al. (2001) *Nat Genet* 29, 83-87 (2001); Griggs, et al. (1995) *Ann Neurol* 38, 705-713 (1995). The disease usually manifests at approximately 20 years of age with foot drop and slowly progressive muscle weakness and atrophy. Histologically, it is associated with muscle fiber degeneration and formation of vacuoles containing 15-18 nm tubulofilaments that immunoreact like β-amyloid, ubiquitin, prion protein and other amyloid-related proteins. Askanas et al. *Curr Opin Rheumatol* 10, 530-542 (1998); Nishino, et al. (2005) *Acta Myol* 24, 80-83 (2005); Askanas, et al. *Ann Neurol* 34, 551-560 (1993); Argov, et al. *Curr Opin Rheumatol* 10, 543-547 (1998). Both weakness and histological changes initially spare the quadriceps. However, the disease is relentlessly progressive, with patients becoming incapacitated and wheelchair-confined within two to three decades. There is no treatment available.

Accordingly, new compositions and methods are needed for treating hereditary inclusion body myopathy and related diseases.

SUMMARY OF THE INVENTION

One aspect of the invention is a therapeutic method for increasing sialic acid in a mammal in need thereof comprising administering to the mammal an effective amount of N-acetyl mannosamine or a derivative thereof to thereby increase sialic acid in the mammal.

In some embodiments, such methods are performed to treat a disease or condition. For example, such a disease can be muscular atrophy or kidney disease. In general, the types of muscular atrophies that can be treated by the methods and compositions of the invention are those caused by sialic acid deficiency. Examples of such muscular atrophy diseases and conditions include distal myopathy with rimmed vacuoles (Nonaka myopathy) and hereditary inclusion body myopathy.

Surprisingly, the compositions and methods of the invention are useful for treating certain kidney conditions and diseases, for example, those involving proteinuria, hematuria resulting primarily or secondarily from hyposialylation (lack of sialic acid). Thus, the present methods are effective for treatment of kidney disorders due to poor kidney membrane formation and/or function. For example, kidney membranes that are affected by loss of sialic acid include the glomerular basement membrane and/or the podocyte membranes. Hence, the invention is useful for treating malformed or poorly functioning glomerular basement membranes and/or podocyte membranes. In general, the methods of the invention can increase sialylation of kidney podocalyxin, improve podocyte foot process morphology and/or improve glomerular basement membrane integrity.

Another aspect of the invention is a method of treating a kidney disorder in a mammal comprising administering a therapeutic amount of N-acetyl mannosamine or a derivative thereof to the mammal, wherein the kidney disorder involves proteinuria and hematuria. For example, such a therapeutic amount of N-acetyl mannosamine or a derivative thereof is about 1 g to about 20 g per day.

DESCRIPTION OF THE FIGURES

FIG. 2A is a schematic diagram illustrating the murine Gne (Ueal) genomic locus, exons 11 and 12, after homologous recombination with the sequence-verified targeting vector. The M712T mutation was created in exon 12, and a neo cassette (under the PGK promoter) flanked by flippase recombinase target (FRT) sites was inserted. LoxP sites were inserted before exon 12 and after the PGK-neo gene. FIG. 2B shows the genotyping of mutant mice. A PCR-amplified 387-bp fragment of genomic DNA across the M712T (ATG to ACG) mutation was digested by the NlaIII restriction endonuclease into 265-bp, 89-bp, and 33-bp fragments in a wild-type allele (+) and into 354-bp and 33-bp fragments in a mutant M712T allele (−). MW, molecular weight. FIG. 2C shows the results of RT-PCR of kidney and skeletal muscle RNA. RNA was reverse transcribed and PCR-amplified using primers covering exons 11 and 12 (355 bp). Digestion by NlaIII cut the wild-type allele (+) into 225-bp, 89-bp, and 41-bp fragments and the mutant M712T allele (−) into 314-bp and 41-bp fragments. Digestion confirmed the exclusive presence of the mutant M712T allele in $Gne^{M712T/M712T}$ (−/−) tissues. FIG. 2D shows the numbers and genotypes of mice at E17-E19 and P21. At P21, genotyping of 76 mice from 13 litters (9 $Gne^{M712T/+}$ matings) identified only 1 $Gne^{M712T/M712T}$ offspring. Subsequent genotyping of 35 E17-E19 embryos from 4 $Gne^{M712T/+}$ mice yielded a Mendelian distribution of genotypes. FIG. 2E shows that at P2, $Gne^{M712T/M712T}$ pups were smaller than their heterozygous ($Gne^{M712T/+}$) and wild-type ($Gne^{+/+}$) littermates and lacked a prominent milkspot.

FIG. 3A illustrates gross kidney pathology. Kidneys of $Gne^{M712T/M712T}$ mice showed hemorrhages but were normal in size and shape compared with kidneys of wild-type ($Gne^{+/+}$) and heterozygous ($Gne^{M712T/+}$) littermates. FIG. 3B shows representative H&E-stained sections of renal cortex (c) and medulla (m) showing tubular dilatations in $Gne^{M712T/M712T}$ mice (arrows). Scale bars: 1,000 μm. FIG. 3C provides high magnification images of collecting ducts, renal tubules, and urinary space, filled with red blood cells in $Gne^{M712T/M712T}$ mice. Scale bars: 100 μm. FIG. 3D provides high magnification images of glomeruli (g) with red blood cells infiltrated into the Bowman space in $Gne^{M712T/M712T}$ mice. Scale bars: 100 μm FIG. 3E shows representative sections of normal glomerulus (DICII, left panel) demonstrating the abundance of Gne/Mnk protein inside the glomerular space upon immunolabeling with Gne/Mnk antibodies (FITC filter, right panel). Scale bars: 50 μm.

FIG. 4A shows representative cross-sections of glomerular capillaries in the juxtamedullar zone of a wild-type mouse (age P2). Enlarged insets (right panels) show detailed endothelial cells (ec), glomerular basement membrane (GBM); arrowheads), and foot processes (fp) of the glomerular epithelial cells (podocytes) with well formed, open filtration slits (asterisks). FIG. 4B shows representative juxtamedullary glomerular capillaries of a $Gne^{M712T/M712T}$ mouse (age P2, littermate of the wild-type mouse shown in FIG. 4A), indicating segmental splitting of the lamina densa of the GBM (arrowheads) as well as dramatically flattened and fused podocyte foot processes lining the GBM. The filtration slits are sparse and irregular in shape and position. Insets (right panels) show fused foot process membranes and formation of abnormal tight junction-like structures at the filtration slits (diamonds). FIGS. 4C and 4D representative glomerular capillaries of a $Gne^{M712T/M712T}$ mouse following ManNAc treatment (age P19). The integrity of the GBM as well as the formation of podocyte foot processes and the number of filtration slits were all improved when compared with the untreated $Gne^{M712T/M712T}$ mouse in FIG. 4B. Some filtration slits were open, while others still formed tight junctions. The GMB showed occasional small stretches of areas where splitting was apparent (arrowheads). L, capillary lumen; N, nucleus; us, urinary space. Scale bars: 1 μm.

FIG. 5A shows the numbers of mice surviving past age P3 after ManNAc administration in the drinking water of $Gne^{M712T/+}$ mice. Six $Gne^{M712T/+}$ mice received 1 mg/ml (~0.2 g/kg/d) ManNAc; 7 total litters were scored; 13 pups died at age P1-P3. Seven $Gne^{M712T/+}$ mice received 5 mg/ml (~1 g/kg/d) ManNAc; 13 total litters were scored; 14 homozygous mutant pups died at age P1-P3. The percentage of survivors of each genotype is indicated. FIG. 5B-5D shows representative H&E-stained kidney sections showing renal cortex and medulla (FIG. 5B); collecting ducts, renal tubules, and urinary space (FIG. 5C); and glomeruli (FIG. 5D) following ManNAc feeding at age P6. Wild-type (Gne+/+) kidneys showed normal histology. $Gne^{M712T/M712T}$ kidneys showed a range from very mild (middle panel) to moderately severe (right panel) red blood cell infiltrations, but in all cases less severe than in untreated $Gne^{M712T/M712T}$ mice at age P2 (FIG. 5E-G). Scale bars: 500 μm (FIG. 5B), 100 mm (FIGS. 5C and 5D). FIG. 5E shows two ManNAc-treated (~1 g/kg/d) 6-week-old male littermates. Surviving homozygous mutant mice ($Gne^{M712T/M712T}$) were smaller than their wild-type littermates. FIG. 5F shows Gne/Mnk epimerase enzymatic activities in skeletal muscle. Administration of ManNAc (shaded bars) increased the activity in wild-type muscle from 100% to 114% (±19.7) (n=3; P=0.2) and increased the activity in homozygous mutant ($Gne^{M712T/M712T}$) muscle from 19.4% (±7.5) to 31% (±8.4) (n=7; P=0.05).

FIG. 6C shows immunoblots of kidney extracts labeled with laminin-1 antibodies. No difference in laminin-1 intensity was detected (n=6; P=0.65) between $Gne^{+/+}$ (+/+) and $Gne^{M712T/M712T}$ (−/−) littermates without or with ManNAc treatment. FIG. 6D shows representative immunoblots of brain extracts labeled with PSA-NCAM antibodies. Upon ManNAc treatment, the intensity of the PSA-NCAM signals, reflecting sialylation status, increased by 2% to 28% in treated $Gne^{M712T/M712T}$ (−/−) brain (n=14) when compared with untreated brain (n=10). FIG. 6E shows immunoblots of kidney extracts (age P2) labeled with antibodies against podocalyxin (~140-150 kDa). Top: Following desialylation of $Gne^{+/+}$ (+/+), $Gne^{M712T/+}$ (+/−), or $Gne^{M712T/M712T}$ (−/−) kidney extracts by neuraminidase (lanes 2 and 4), podocalyxin migrated more slowly (~160-180 kDa) than untreated samples (lanes 1 and 3). $Gne^{M712T/M712T}$ (−/−) kidney extracts (lanes 5 and 6) contained desialylated podocalyxin. Bottom: Sialylation of podocalyxin at P6 in $Gne^{M712T/M712T}$ (−/−) mice changed significantly after ManNAc treatment (lanes 3 and 4).

DETAILED DESCRIPTION OF THE INVENTION

Figure 1:
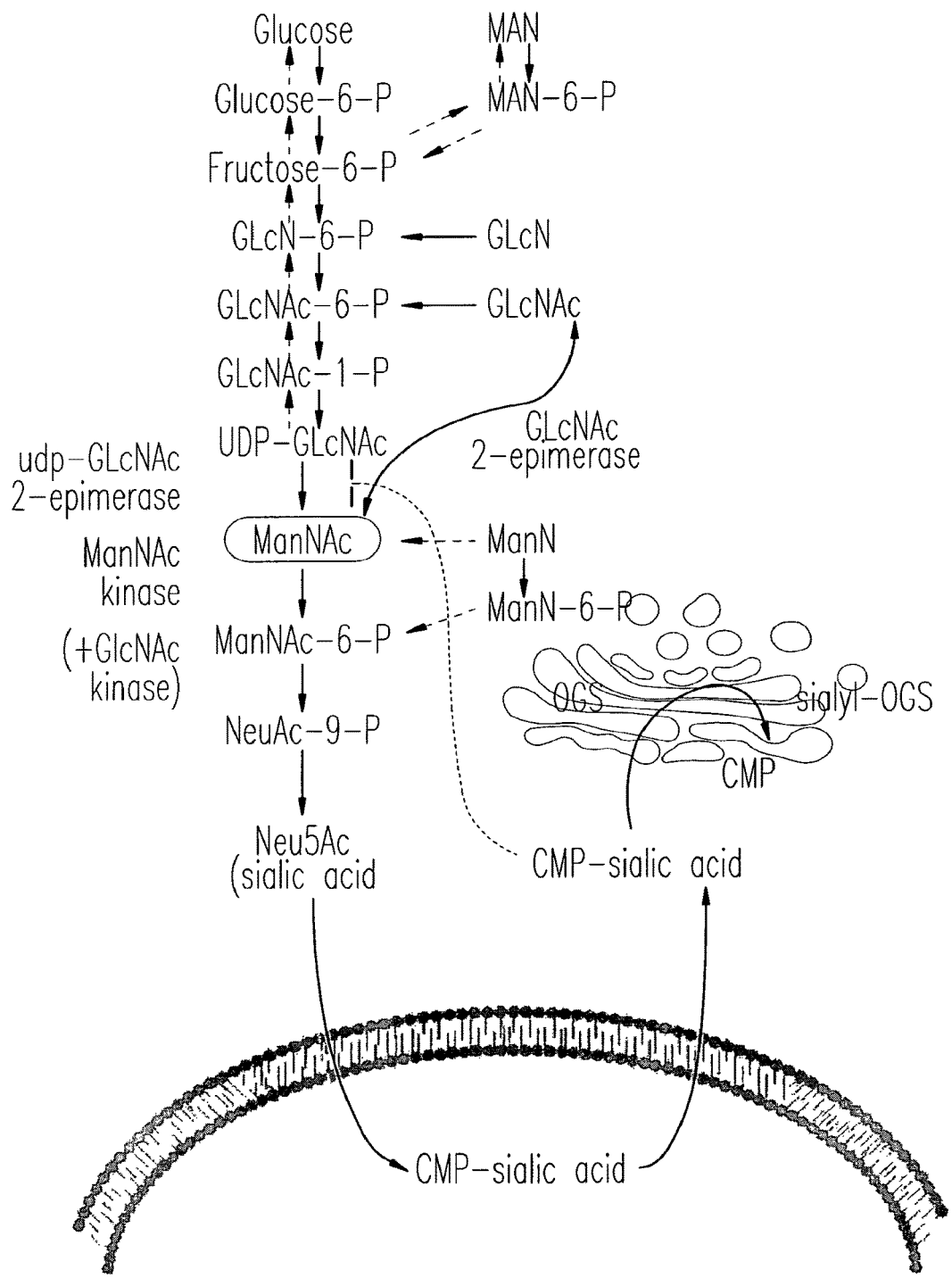
FIG. 1 schematically illustrates the intracellular metabolism of sialic acid. This figure shows portions of a cell, where the nucleus is depicted at the bottom (below the depicted nuclear membrane) and the cytoplasm is at the top of the figure. Cytosolic glucose is converted in several steps into UDP-GlcNAc, which serves as substrate for the bi-functional, rate-limiting, committed enzyme for sialic acid biosynthesis: UDP-GlcNAc 2-epimerase/ManNAc kinase (GNE/MNK). GNE catalytic activity (EC 5.1.3.14) epimerizes UDP-GlcNAc to ManNAc, followed by the phosphorylation of ManNAc to ManNAc-6-phosphate (MaNAc-6-P) by the MNK kinase catalytic domain (EC 2.7.1.60). ManNAc-6-phosphate is then condensed with phosphoenolpyruvate to Neu5Ac-9-phosphate by Neu5Ac-9-P synthetase. The phosphate is then released and Neu5Ac is activated by CMP-Neu5Ac synthetase to CMP-Neu5Ac in the nucleus. CMP-Neu5Ac then enters the trans-Golgi and serves as the substrate for different sialyltransferases involved in the production of sialylated glycoconjugates. These are subsequently cleaved in the lysosome to yield free sialic acid, which is exported to the cytoplasm and re-utilized or degraded to ManNAc and pyruvate. CMP-sialic acid strongly feedback inhibits the GNE epimerase at its allosteric site.

According to the invention, N-acetyl-mannosamine and derivatives thereof are useful for treating a variety of diseases and conditions. N-acetyl-D-mannosamine is a key compound in the sialic acid biosynthetic pathway (see FIG. 1). In particular, there is a regulated, rate-limiting enzymatic step in the pathway that leads to sialic acid formation, and this rate-limiting step gives rise to N-acetyl-D-mannosamine. Hence, once N-acetyl-D-mannosamine is formed or administered, no other enzymatic step leading to the formation of sialic acid is subject to feedback inhibition. Thus, administration of N-acetyl-D-mannosamine will lead to increased amounts of sialic acid. The structure of N-acetyl-mannosamine is shown below.

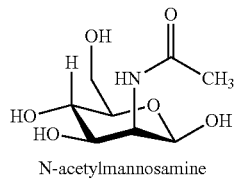

N-acetylmannosamine

Therefore, according to the invention, administration of N-acetyl mannosamine (ManNAc) and/or its derivatives promotes formation of sialic acid (N-acetylneuramic acid). Sialic acids are sugars found on many cellular and tissue components. For example, sialic acids are present on most cell surfaces, and on proteins and lipids and are involved in cell to cell interactions. Sialic acid-rich oligosaccharides on the glycoconjugates found on surface membranes help keep water at the surface of cells. The sialic acid-rich regions also contribute to creating a negative charge on the cells surface. Since water is a polar molecule, it is attracted to cell surfaces and membranes. Thus, sialic acids contribute to cellular hydration and fluid uptake. Sialic acid is also a vital component of many body fluids including, serum, cerebrospinal, saliva, amniotic, and mother's milk.

N-Acetylmannosamine Derivatives

According to the invention, N-acetylmannosamine and derivatives thereof can also be used in the therapeutic methods and compositions of the invention. The structures of such N-acetylmannosamine derivatives useful in the invention are defined by Formula I.

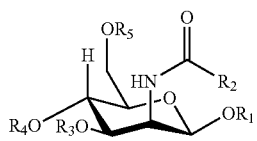

wherein:

$R_1$, $R_3$, $R_4$, or $R_5$ is hydrogen, lower alkanoyl, carboxylate or lower alkyl; and $R_2$ is lower alkyl, lower alkanoylalkyl, lower alkyl alkanoyloxy.

The following definitions are used, unless otherwise described: Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

Lower alkyl refers to $(C_1-C_6)$alkyl. Such a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$ cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1- hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$ alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

Therapeutic Methods

According to the invention, N-acetyl-D-mannosamine (ManNAc) and derivatives thereof are useful therapeutic agents for increasing production of sialic acids in mammals, and such increased production of sialic acid has profound therapeutic benefits. Sialic acids are important for proper development and functioning of many organs and tissues, and a deficiency of sialic acid can give rise to many different types of diseases and conditions. For example, abnormalities of sialic acid metabolism cause a severe infantile disease (infantile sialic acid storage disease, ISSD), characterized by failure to thrive, hepatosplenomegaly, coarse facial features, severe mental and motor retardation presenting at birth and often leading to death within the first year of life, or diseases of later onset (Salla disease, sialuria).

As shown herein, administration of ManNAc (and derivatives thereof) is useful for treating myopathies, muscular atrophy and/or muscular dystrophy (e.g., hereditary inclusion body myopathy (HIBM)) and kidney conditions and diseases (e.g., those involving proteinuria and hematuria).

Myopathies that can be treated with the present compositions and methods also include distal myopathy with rimmed vacuoles (Nonaka myopathy) and the muscular dystrophy hereditary inclusion body myopathy (HIBM).

Proteinuria involves leakage of protein from the blood into the urine. If the amount of protein in the urine is very high, this condition is often called nephrotic syndrome. While there may be many causes for nephritic syndrome, according to the invention at least one cause is a deficiency of sialic acid, which has a direct impact on the formation, structure and function of kidney glomeruli and the membranes associated therewith. Several types of diseases exhibit the symptoms of proteinuria, including high blood pressure, infections, reflux nephropathy, diabetes, various types of glomerulonephritis, including minimal change nephrosis. However, by improving the structure and function of nephron components that require sialic acid, the present compositions and methods can treat any of these diseases. Thus, for example, the methods and compositions of the invention dramatically improve kidney function by improving the structure and filtration properties of kidneys, thereby reducing the amount of protein in the urine and/or the severity or progression of proteinuria.

Hematuria simply means blood in the urine. The blood may be visible, so that the urine appears reddish or darker than normal (called gross hematuria). If the blood is invisible and is discovered only when a urine sample is examined in a laboratory urine test, the condition is called microscopic hematuria. In general, hematuria is more a symptom than a condition in itself, because it has many possible causes. A urinary tract infection, kidney or bladder stones, an enlarged prostate in men, cystitis (a bladder infection, usually in women) or bladder, kidney or prostate cancer can all cause hematuria. Other causes include injuries that result in a bruised kidneys; sickle cell anemia and other abnormal red blood cell diseases; and certain medications, such as blood thinners (e.g., aspirin and some other pain relief medicines). More specific causes of glomerular basal membrane dysfunction, such as Alport disease, thin membrane disease, and IgA nephropathy, may particularly improve when the treatment methods described herein are employed.

In general, the treatment methods of the invention involve administering to a mammal (or patient) a therapeutically effective amount of N-acetyl mannosamine and/or a derivative thereof. Such a therapeutically effective amount is generally given daily for appropriate periods of time. Effective amounts for human patients are, for example, about 0.1 g/day to about 50 g/day, of about 0.2 g/day to about 25 g/day, from about 0.3 g/day to about 12 g/day, from about 0.4 g/day to about 10 g/day, from about 0.5 g/day to about 8 g/day, and from about 0.7 g/day to about 6 g/day. Generally, N-acetyl mannosamine and/or a derivative thereof is administered for periods of time sufficient to increase the amount of sialic acid in the mammal and thereby achieve a therapeutic benefit. Therapeutic benefits that can be achieved by administration of N-acetyl mannosamine and/or a derivative thereof include improved kidney function, reduction in protein excretion in the urine, reduction in blood concentrations in the urine, increased sialylation of podocalyxin, increased sialylation of PSA-NCAM (and/or other tissue specific target glycoproteins), fewer cystic tubular dilatations in the kidney cortex and in the kidney medulla, less fusion and flattening of the podocyte foot processes, greater number of open slit diaphragms in the kidneys, improvement in the "finger shaping" of the kidney foot processes, improved overall integrity of the GBM, increased Gne/Mnk protein expression and Gne-epimerase activities.

ManNAc is a ubiquitous but rare monosaccharide involved in a range of metabolic processes. It is uncharged and crosses membranes readily. ManNAc is a constituent of numerous glycolipids and glycoproteins, and is the first committed precursor for the biosynthesis of N-acetylneuraminic (Neu5Ac, or sialic acid), which consists of N-acetyl-D-mannosamine in an ether linkage with D-pyruvic acid. ManNAc is formed from UDP-N-acetylglucosamine (UDP-GlcNAc) by the action of UDP-GlcNAc 2-epimerase. ManNAc is then phosphorylated by a specific kinase to ManNAc-6-P (FIG. 1). ManNAc is situated in the sialic acid biosynthesis pathway after the regulated, rate-limiting GNE step (FIG. 1), so its metabolism is not subject to feedback inhibition. Residual MNK activity in HIBM patients, or ancillary kinases such as GlcNAc kinase (Hinderlich et al. *Eur. J. Biochem.* 252: 133-139 (1998)), might convert ManNAc into ManNAc-6-phosphate for subsequent synthesis of sialic acid. In fact, hyposialylated, Gne-deficient mouse embryonic stem cells became resialylated after their growth medium was supplemented with ManNAc (Schwarzkopf et al. *Proc. Natl. Acad. Sci. U.S.A.* 99: 5267-70 (2002)). Furthermore, incubation of cultured cells with "unnatural" ManNAc derivatives, i.e., N-levulinoylmannosamine (ManLev) or N-azidoacetyl-mannosamine (ManNAz), resulted in incorporation of the downstream sialic acid analogs (SiaLev or SiaNAz) into cell surface glycoconjugates (Charter et al. *Glycobiology* 10: 1049-56 (2000)).

Hereditary Inclusion Body Myopathy (HIBM)

Studies of an Iranian-Jewish genetic isolate (Argov, et al., *Neurology* 60, 1519-1523 (2003)) indicate that HIBM is mapped to chromosome 9p12-13. The causative gene for HIBM is GNE, coding for the bifunctional enzyme UDP-N-acetylglucosamine-2-epimerase/N-acetylmannosamine kinase. Eisenberg, et al. (2001) *Nat Genet* 29, 83-87 (2001); Tanner, M. E., *Bioorg Chem* 33, 216-228 (2005); Stasche, et al. *J Biol Chem* 272, 24319-24324 (1997); Hinderlich, et al. *J Biol Chem* 272, 24313-24318 (1997); Jacobs, et al. *Biochemistry* 40, 12864-12874 (2001). The function and feedback regulation of GNE/MNK is depicted in FIG. 1. Distal Myopathy with Rimmed Vacuoles (DMRV) is a Japanese variant, allelic to HIBM. Nishino et al. *Neurology* 59, 1689-1693 (2002); Kayashima et al. *J Hum Genet* 47, 77-79 (2002); Hinderlich, et al. *Neurology* 61, 145 (2003). Nearly twenty GNE mutations have been reported in HIBM patients from different ethnic backgrounds, with founder effects among the Iranian Jews and Japanese. Broccolini , et al. *Hum Mutat* 23, 632 (2004); Eisenberg, et al. *Hum Mutat* 21, 99 (2003); Tomimitsu, et al. *Neurology* 59, 451-454 (2002); Darvish, et al. *Mol Genet Metab* 77, 252-256 (2002). The mutations causing HIBM occur in the regions encoding either the epimerase domain or the kinase domain. Most are missense mutations and result in decreased enzyme GNE activity and underproduction of sialic acid. Sparks, et al. *Glycobiology* 15, 1102-1110 (2005); Penner, et al. *Biochemistry* 45, 2968-2977 (2006).

Sialic acids are negatively charged terminal sugar moieties added during the post-translational modification on oligosaccharide chains of proteins and lipids to create glycoproteins and glycolipids. Varki, *Faseb J* 11, 248-255 (1997); Varki et al. *Anal Biochem* 137, 236-247 (1984). They act as molecular determinants of specific biological processes such as cellular adhesion, cell-cell interactions and signal transduction. Schauer, *Glycoconj J* 17, 485-499 (2000); Kelm et al. *Int Rev Cytol* 175, 137-240 (1997).

The pathophysiology of HIBM remains largely unknown, but the dysfunction in GNE suggests that impaired sialylation of glycoproteins is involved. Such a defect could influence cell-cell interactions, intracellular trafficking, organelle biogenesis, apoptosis and secretion. In fact, UDP-GlcNAc 2-epimerase regulates sialylation of cell surface molecules (Keppler et al. *Science* 284: 1372-76 (1999)), and sialylation appears to be critical for mouse development (Schwarzkopf et al. *Proc Natl Acad Sci USA* 99, 5267-5270 (2002)).

One hypothesis for the pathophysiology of HIBM involves undersialylation of α-DG, an essential component of the dystrophin-glycoprotein complex. Michele et al. *Nature* 418, 417-422 (2002); Michele et al. *J Biol Chem* 278, 15457-15460 (2003). α-DG is heavily glycosylated with O-mannosyl glycans (mannose-N-acetylglucosamine-galactose-sialic acid) linked to a serine or threonine; these glycans are critical for α-DG's interactions with laminin and other extracellular ligands. Aberrant glycosylation of α-DG is the underlying biochemical defect in several congenital muscular dystrophies, generally termed "dystroglycanopathies," including Fukuyama's congenital muscular dystrophy, Muscle-Eye-Brain disease, Walker-Warburg syndrome and the congenital muscular dystrophies type C1C and C1D. Martin et al., *Glycobiology* 13, 67R-75R (2003); Martin-Rendon, et al. *Trends Pharmacol Sci* 24, 178-183 (2003). The inventors and others have shown variable hyposialylation of α-DG and other glycoproteins, such as Neural Crest Adhesion Molecule (NCAM), in HIBM. Huizing et al. *Mol Genet Metab* 81, 196-202 (2004); Savelkoul et al. *Mol Genet Metab* 88, 389-390 (2006); Sparks et al. *BMC Neurol* 7, 3 (2007); Broccolini et al. *Neuromuscul Disord* 15, 177-184 (2005); Ricci et al. *Neurology* 66, 755-758 (2006); Salama et al. *Biochem Biophys Res Commun* 328, 221-226 (2005); Tajima et al. *Am J Pathol* 166, 1121-1130 (2005).

However, prior to the present invention, the basic pathogenic mechanisms of HIBM, an HIBM animal model, and an effective therapy for HIBM were lacking. These issues are addressed by the present invention through creation of a Gne gene-targeted knockin mouse mimicking the M712T mutation of Iranian-Jewish HIBM patients and through studies using this knockin mouse model that have defined effective therapeutic methods.

A sequence for the mouse Gne protein is shown below (SEQ ID NO:1).

```
  1 MEKNGNNRKL RVCVATCNRA DYSKLAPIMF GIKTEPAFFE
 41 LDVVVLGSHL IDDYGNTYRM IEQDDFDINT RLHTIVRGED
 81 EAAMVESVGL ALVKLPDVLN RLKPDIMIVH GDRFDALALA
121 TSAALMNIRI LHIEGGEVSG TIDDSIRHAI TKLAHYHVCC
161 TRSAEQHLIS MCEDHDRILL AGCPSYDKLL SAKNKDYMSI
201 IRMWLGDDVK CKDYIVALQH PVTTDIKHSI KMFELTLDAL
241 ISFNKRTLVL FPNIDAGSKE MVRVMRKKGI EHHPNFRAVK
281 HVPFDQFIQL VAHAGCMIGN SSCGVREVGA FGTPVINLGT
321 RQIGRETGEN VLHVRDADTQ DKILQALHLQ FGKQYPCSKI
361 YGDGNAVPRI LKFLKSIDLQ EPLQKKFCFP PVKENISQDI
401 DHILETLSAL AVDLGGTNLR VAIVSMKGEI VKKYTQFNPK
441 TYEERISLIL QMCVEAAAEA VKLNCRILGV GISTGGRVNP
481 QEGVVLHSTK LIQEWNSVDL RTPLSDTLHL PVWVDNDGNC
521 AAMAERKFGQ GKGQENFVTL ITGTGIGGGI IHQHELIHGS
561 SFCAAELGHL VVSLDGPDCS CGSHGCIEAY ASGMALQREA
601 KKLHDEDLLL VEGMSVPKDE AVGALHLIQA AKLGNVKAQS
641 ILRTAGTALG LGVVNILHTM NPSLVILSGV LASHYIHIVK
681 DVIRQQALSS VQDVDVVVSD LVDPALLGAA SMVLDYTTRR
721 IH
```

When this Gne protein has the M712T mutation, the sequence for Gne mutant protein arising from the Gne$^{M712T}$ mutation is as follows (SEQ ID NO:2), where the methionine at position 712 has been changed to a threonine (bold and underlined amino acid shown below).

```
  1 MEKNGNNRKL RVCVATCNRA DYSKLAPIMF GIKTEPAFFE
 41 LDVVVLGSHL IDDYGNTYRM IEQDDFDINT RLHTIVRGED
 81 EAAMVESVGL ALVKLPDVLN RLKPDIMIVH GDRFDALALA
121 TSAALMNIRI LHIEGGEVSG TIDDSIRHAI TKLAHYHVCC
161 TRSAEQHLIS MCEDHDRILL AGCPSYDKLL SAKNKDYMSI
201 IRMWLGDDVK CKDYIVALQH PVTTDIKHSI KMFELTLDAL
241 ISFNKRTLVL FPNIDAGSKE MVRVMRKKGI EHHPNFRAVK
281 HVPFDQFIQL VAHAGCMIGN SSCGVREVGA FGTPVINLGT
321 RQIGRETGEN VLHVRDADTQ DKILQALHLQ FGKQYPCSKI
361 YGDGNAVPRI LKFLKSIDLQ EPLQKKFCFP PVKENISQDI
401 DHILETLSAL AVDLGGTNLR VAIVSMKGEI VKKYTQFNPK
441 TYEERISLIL QMCVEAAAEA VKLNCRILGV GISTGGRVNP
481 QEGVVLHSTK LIQEWNSVDL RTPLSDTLHL PVWVDNDGNC
521 AAMAERKFGQ GKGQENFVTL ITGTGIGGGI IHQHELIHGS
561 SFCAAELGHL VVSLDGPDCS CGSHGCIEAY ASGMALQREA
601 KKLHDEDLLL VEGMSVPKDE AVGALHLIQA AKLGNVKAQS
641 ILRTAGTALG LGVVNILHTM NPSLVILSGV LASHYIHIVK
681 DVIRQQALSS VQDVDVVVSD LVDPALLGAA STVLDYTTRR
721 IH
```

Figure 2A:
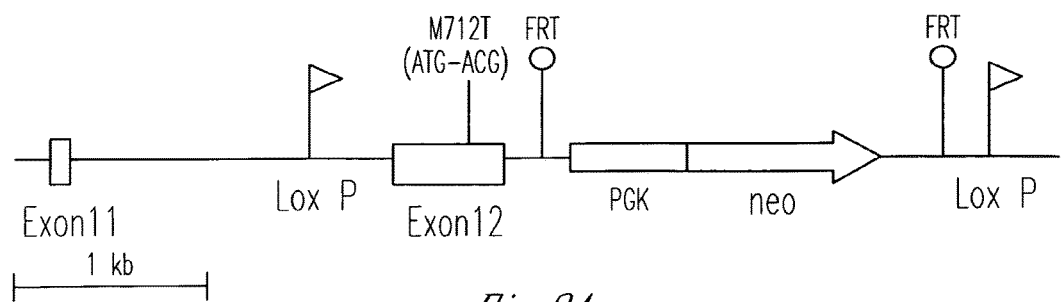
FIG. 2A-E illustrates the generation and identification of GneM712T/M712T knockin mice.
Figure 2B:
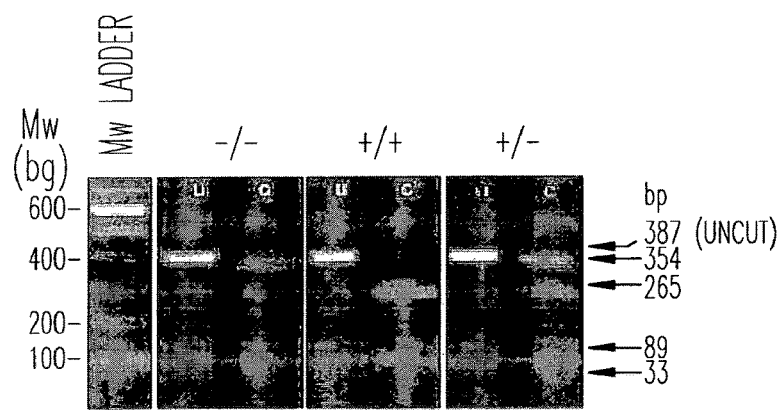
Figure 2C:
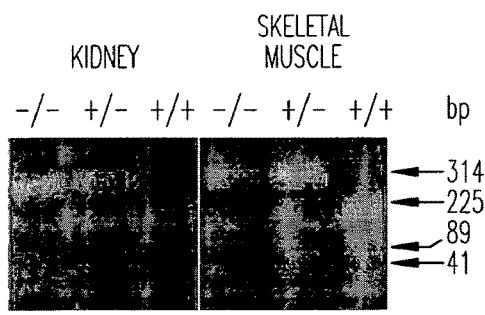
Figure 2D:
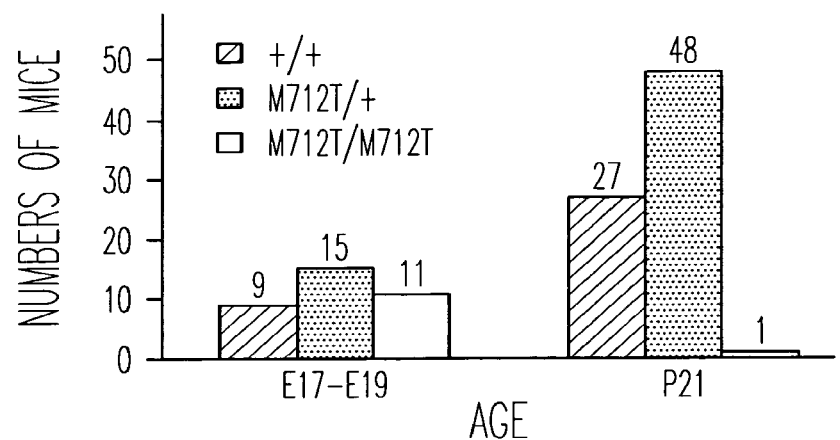
Figure 5A:
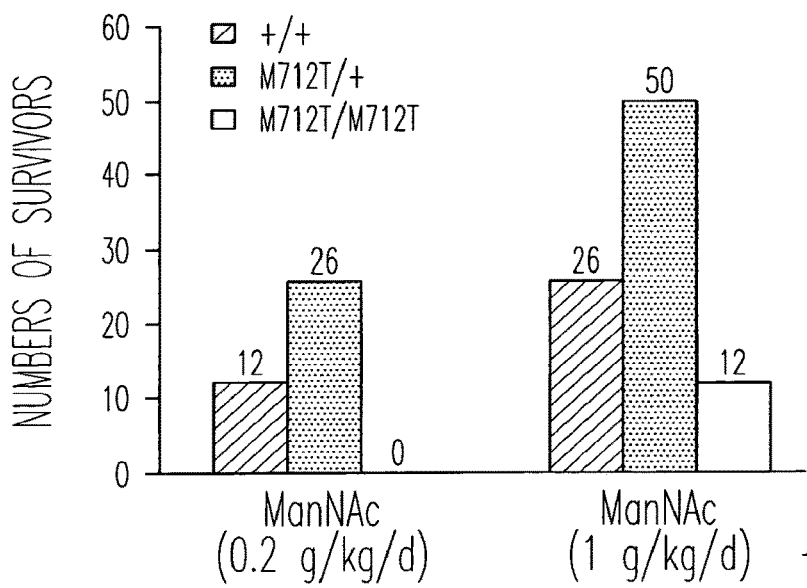
FIG. 5A-5F illustrates the biochemistry and renal histology of knockin mice following ManNAc treatment.
Figure 5B:
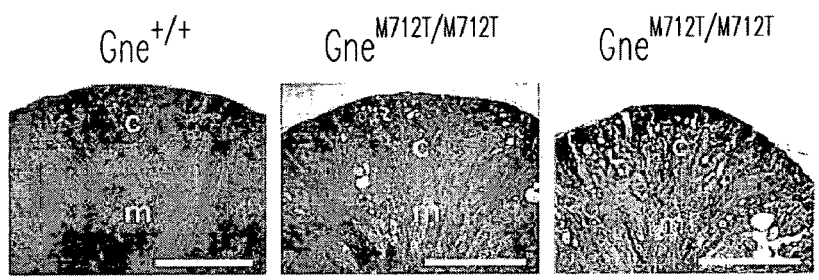
Figure 5C:
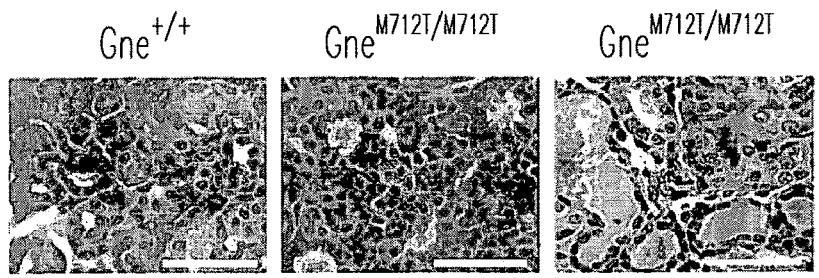
Figure 5D:
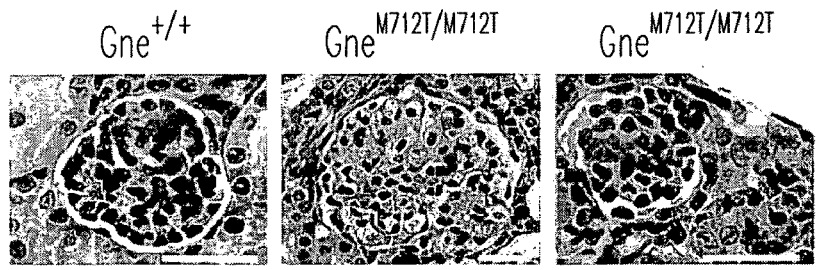
Figure 5E:
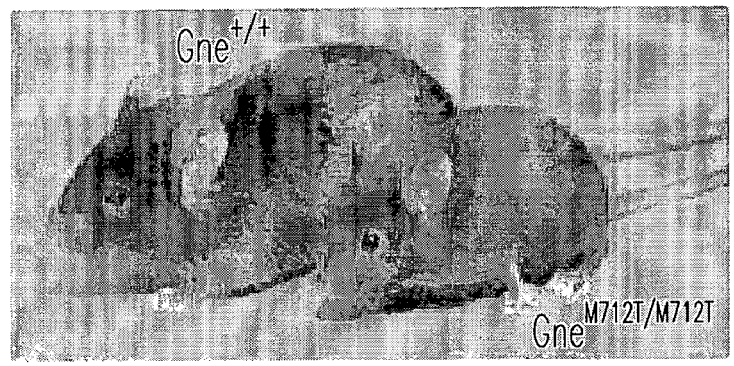
Figure 5F:
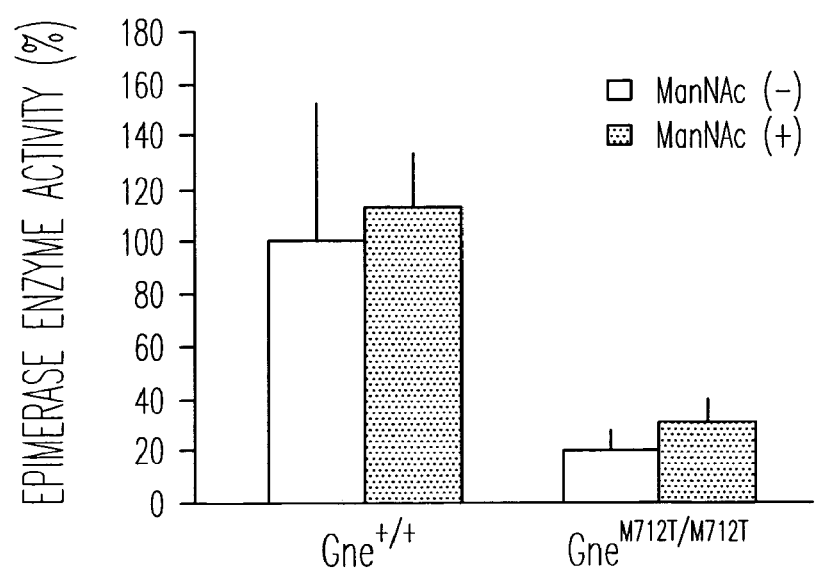

Although this M712T mutation gives rise to a recessive phenotype, it has dramatic effects upon the survival and physiology of mammals. For example, HIBM exhibits non life-threatening symptoms in humans that emerge in adulthood and lead to slowly progressive muscle weakness. Most patients develop symptoms while in their early 20s and become wheelchair-bound by the time they reach 40, as their arm, hand, leg and core muscles progressively weaken. The symptoms in mice are even more dramatic. For example, upon mating nine pairs of Gne$^{M712T/+}$ mice, 101 progeny were obtained. Of those 101 progeny 26 homozygous mutated (Gne$^{M712T/M712T}$) mice were produced. However, only one male with the Gne$^{M712T/M712T}$ genotype survived past age P3 (FIG. 2D). The remaining 25 Gne$^{M712T/M712T}$ homozygous mutated offspring died at age P1-P3. This lone surviving mouse showed no muscle pathology at age P2. The lack of early myopathic features recapitulates the human HIBM phenotype. In both mice and humans, the muscle pathology occurs late or is attenuated likely by a modicum of sialic acid is provided through the actions of residual Gne/Mnk enzymatic activities (Sparks et al. *Glycobiology* 15: 1102-10 (2005); Noguchi et al. *J. Biol. Chem.* 279: 11402-407 (2004)) (FIG. 5F and FIGS. 6, A and B).

Kidney Conditions

Instead of early-onset muscle problems, homozygous Gne$^{M712T/M712T}$ mice exhibit early signs of severe glomerular hematuria and podocytopathy, including effacement of the podocyte foot processes and segmental splitting of the glomerular basement membrane (GBM), likely due to hyposialylation of specific membrane glycoproteins. Unexpectedly, the Gne$^{M712T/M712T}$ knockin mice provide a novel animal model of podocytopathy and/or segmental splitting of the GBM, demonstrating the significance of sialic acid synthesis in kidney development and function. Structural elements in the kidney that are important for filtering waste from the blood are severely impaired by the sialic acid deficiency. This outcome demonstrates the significance of the ability of the body to synthesize sialic acid for kidney development and function.

As shown in the Examples and Figures of this application, administration of ManNAc to pregnant mice had a remarkably salutary effect on the survival and renal development of homozygous pups. In particular, ManNAc administration was associated with increased enzymatic activity of Gne, increased sialylation of kidney podocalyxin, and improved morphology of the podocyte foot processes and GBM integrity.

Therefore, according to the invention, ManNAc is effective not only as a treatment for HIBM but also for treatment of kidney disorders. Thus, ManNAc may be used to treat podocytopathies, minimal change nephrosis, focal and segmental glomerulosclerosis, membranous glomerulonephritis, and other forms of unexplained idiopathic nephrotic syndrome, as well as glomerular basement membrane diseases such as Alport disease and thin membrane disease. Such kidney disorders and conditions are sometimes characterized by segmental splitting of the glomerular basement membrane and/or podocytopathy due to disturbed polyanions on podocyte membranes, or to changes in the amount or charge (sialylation) of glomerular basement membrane components.

Formulations and Administration

N-acetyl mannosamine and/or derivatives thereof are administered so as to achieve a reduction in at least one symptom associated with an indication or disease. For example, administration of N-acetyl mannosamine and/or derivatives thereof can lead to a reduction in proteinuria (e.g., lower amounts of protein in the urine), a reduction in hematuria (e.g., lower amounts of red blood cells in the urine) and improvement of muscle function (e.g., in patients with muscular atrophy).

To achieve the desired effect(s), N-acetyl mannosamine and/or derivatives thereof may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 200 to 400 mg/kg or at least about 1 mg/kg to about 25 to 200 mg/kg of body weight, although other dosages may provide beneficial results. The amount administered will vary depending on various factors including, but not limited to the disease, the weight, the physical condition, the health, the age of the mammal, whether prevention or treatment is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of N-acetyl mannosamine and/or derivatives thereof may be essentially continuous over a pre-selected period of time or may be in a series of spaced doses. Both local and systemic administration is contemplated.

To prepare the composition, N-acetyl mannosamine and/or one or more derivatives thereof are synthesized or otherwise obtained, and purified as necessary or desired. N-acetyl mannosamine (and/or derivatives thereof) can then be added to a composition (or food product), adjusted to the appropriate concentration, and optionally combined with other agents. The absolute weight of N-acetyl mannosamine and/or its derivatives that is included in a unit dose can vary widely. For example, about 0.01 to about 2 g, or about 0.1 to about 1 g of N-acetyl mannosamine and/or derivatives thereof are often used in compositions. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of N-acetyl mannosamine and/or derivatives thereof can vary as well. Such daily doses can range, for example, from about 0.1 g/day to about 50 g/day, from about 0.2 g/day to about 25 g/day, from about 0.3 g/day to about 12 g/day, from about 0.4 g/day to about 10 g/day, from about 0.5 g/day to about 8 g/day, and from about 0.7 g/day to about 6 g/day.

Thus, one or more suitable unit dosage forms comprising N-acetyl mannosamine and/or derivatives thereof can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing N-acetyl mannosamine and/or derivatives thereof with liquid carriers, solid matrices, semi-solid carriers, finely divided solid carriers or combinations thereof, and then, if necessary, introducing or shaping the product into the desired delivery system.

When N-acetyl mannosamine and/or its derivatives is prepared for oral administration, it is generally combined with a pharmaceutically acceptable carrier, diluent or excipient to form a pharmaceutical formulation, or unit dosage form. For oral administration, N-acetyl mannosamine (and/or derivatives thereof) may be present as a powder, a granular formulation, a solution, a suspension, an emulsion or in a natural or synthetic polymer or resin for ingestion of N-acetyl mannosamine (and/or one or more derivatives thereof) from a chewing gum. The active ingredients may also be presented as a bolus, electuary or paste. Orally administered N-acetyl mannosamine and/or derivatives thereof can also be formulated for sustained release. For example, N-acetyl mannosamine and/or derivatives thereof can be coated, micro-encapsulated, or otherwise placed within a sustained delivery device, for example, in order to avoid salivary bacteria degradation. The total N-acetyl mannosamine and its derivatives in such formulations comprises from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing N-acetyl mannosamine and/or derivatives thereof can be prepared by procedures known in the art using well-known and readily available ingredients. For example, N-acetyl mannosamine and/or its derivatives can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing N-acetyl mannosamine (and/or its derivatives) can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing N-acetyl mannosamine (and/or its derivatives) can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing N-acetyl mannosamine and/or its derivatives are designed to resist disintegration in the stomach and dissolve in the more neutral to alkaline environment of the duodenum.

N-acetyl mannosamine and/or its derivatives can also be formulated as an elixir or solution for convenient oral administration or as a solution appropriate for parenteral administration, for instance by intramuscular, subcutaneous, intraperitoneal or intravenous routes. The pharmaceutical formulations of N-acetyl mannosamine and/or its derivatives can also take the form of an aqueous or anhydrous solution or dispersion, or alternatively the form of an emulsion or suspension or salve.

Thus, N-acetyl mannosamine and/or its derivatives may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The N-acetyl mannosamine, its derivatives and other ingredients may form suspensions, solutions, or emulsions in oily or aqueous vehicles, and may contain formulatory agents such as suspending, stabilizing and/or dispersing agents. Alternatively, the N-acetyl mannosamine, its derivatives and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add other ingredients such as antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, N-acetyl mannosamine and/or derivatives thereof are well suited to formulation in a sustained release dosage form. Thus, such formulations can be so constituted that they release the N-acetyl mannosamine and/or its derivative, for example, in a particular part of the intestinal, urogenital or respiratory tract, over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, N-acetyl mannosamine and/or its derivative(s) may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, N-acetyl mannosamine and/or its derivatives can be delivered via patches or bandages for dermal administration. Alternatively, N-acetyl mannosamine and/or its derivatives can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The therapeutic agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with N-acetyl mannosamine and/or derivatives thereof in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

N-acetyl mannosamine and/or its derivatives may further be formulated for topical administration in the mouth or throat. For example, N-acetyl mannosamine and/or its derivatives may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art.

Furthermore, N-acetyl mannosamine and/or its derivatives may also be used in combination with other therapeutic agents, for example, pain relievers, anti-inflammatory agents, and the like, whether for the conditions described or some other condition.

The present invention further pertains to a packaged pharmaceutical composition such as a kit or other container for increasing production of sialic acid in a mammal. The kit or container holds a therapeutically effective amount of a pharmaceutical composition for increasing intracellular production of sialic acid and instructions for using the pharmaceutical composition for increasing production of sialic acid in the mammal. The pharmaceutical composition includes N-acetyl mannosamine and/or its derivatives in a therapeutically effective amount such that sialic acid production is increased.

Food Supplement

According to the invention, N-acetyl mannosamine and/or its derivatives can be administered as a food supplement or incorporated into food or drink item such as a nutritional bar, snack bar, cookie, candy, cereal, pudding, ice cream, frozen confectionary, chewing gum, drink mix, soda pop, liquid supplement, sauce, salad dressing, gravy, jelly, jam, spread, margarine, peanut butter, nut spread, frosting, and the like. In essence, can be used in any food, composition or supplement in which sugar is employed. Hence, N-acetyl mannosamine and/or derivatives thereof can be used as a partial or full substitute for sugar.

Such food supplements, drinks and food items can include any other food ingredient including, for example, flour, oil, cream, butter, sugar, salt, spices and the like. In addition, the food supplements, drinks and food items can include vitamins and nutrients commonly found in other nutritional supplements.

Having now generally described the invention, the same will be more readily understood through reference to the following examples which are provided by way of illustration, and are not intended to be limiting of the present invention.

EXAMPLE 1

ManNAc Administration is Useful for Treating HIBM and Renal Disorders

This Example shows that ManNAc may be a useful treatment not only for HIBM but also for renal disorders involving proteinuria and hematuria due to podocytopathy and/or segmental splitting of the glomerular basement membrane.

Methods $Gne^{M712T/M712T}$ mice. $Gne^{M712T/M712T}$ knockin mice were generated by targeting the M712T (ATG to ACG) mutation of exon 12 of the murine Gne gene (Gne, Uae1, GenBank NM_015828) (FIG. 2A). The nucleotide sequence for this Gne, Uae1 allele (GenBank NM_015828) without the mutation is shown below for easy reference (SEQ ID NO:3).

```
   1 GCTAAACCAG AGGCCAGACG GCAGCTCAGG AGTCCGACCA
  41 CACCTCAGGA AACAGCTGTG CCACAGGATG GAAACACACG
  81 CGCATCTCCA CAGGGAGCAG AGCTACGCAG GACCTCATGA
 121 ACTCTATTTT AAGAAACTCT CAAGTAAAAA GAAGCAAGTC
 161 ATGGAGAAGA ACGGGAACAA CCGAAAGCTC CGGGTTTGCG
 201 TTGCCACCTG CAACCGAGCT GACTACTCCA AACTGGCCCC
 241 GATCATGTTC GGCATCAAGA CAGAGCCCGC GTTCTTTGAG
 281 TTGGACGTGG TGGTGCTCGG CTCCCACCTG ATTGACGACT
 321 ATGGAAACAC ATACCGCATG ATTGAGCAAG ATGACTTTGA
 361 CATTAACACC AGGCTCCACA CGATTGTTAG AGGGGAAGAT
 401 GAAGCGGCCA TGGTAGAGTC GGTAGGCCTA GCGCTCGTGA
 441 AGCTACCGGA CGTCCTCAAT CGCCTGAAGC CCGACATCAT
 481 GATTGTTCAC GGAGACCGAT TTGACGCCCT TGCTCTGGCT
 521 ACGTCTGCTG CCTTGATGAA CATCCGCATC CTTCACATTG
 561 AAGGAGGCGA GGTCAGCGGG ACCATTGATG ACTCTATCAG
 601 ACACGCCATA ACAAACTGG CTCACTACCA TGTGTGCTGC
 641 ACTAGAAGTG CAGAGCAGCA CCTGATCTCT ATGTGCGAGG
 661 ACCACGACCG CATCCTGTTG GCAGGCTGCC CTTCCTATGA
 721 CAAACTGCTC TCCGCCAAGA ACAAAGACTA TATGAGCATC
 761 ATTCGGATGT GGCTAGGCGA TGATGTAAAA TGTAAGGATT
 801 ACATCGTTGC CCTGCAGCAT CCCGTGACCA CTGACATTAA
 841 GCATTCCATA AAGATGTTTG AGCTAACACT GGATGCCCTG
 881 ATCTCGTTTA ACAAGAGGAC CCTAGTTCTG TTTCCAAATA
 921 TCGATGCAGG CAGCAAGGAG ATGGTTCGAG TGATGCGGAA
 961 GAAGGGCATC GAGCATCACC CCAATTTCCG TGCAGTCAAG
1001 CACGTCCCGT TGACCAGTT CATACAGCTG GTCGCCCACG
1041 CTGGCTGCAT GATTGGGAAT AGCAGCTGCG GCGTGCGAGA
1081 GGTTGGCGCT TTCGGAACAC CCGTGATCAA CCTGGGCACA
1121 AGGCAGATAG GAAGAGAAAC CGGGGAGAAT GTTCTTCATG
```

```
-continued
1161 TCAGGGATGC TGACACCCAA GATAAAATAT TGCAAGCACT

1201 ACACCTCCAG TTCGGCAAAC AGTACCCTTG CTCAAAGATA

1241 TATGGGGATG GGAATGCTGT TCCAAGGATT TTAAAGTTTC

1281 TCAAATCCAT TGACCTTCAA GAGCCACTAC AGAAGAAATT

1321 CTGCTTCCCC CCTGTAAAGG AGAACATCTC TCAAGACATT

1361 GACCACATCC TGGAAACTCT GAGTGCCTTG GCTGTTGATC

1401 TTGGCGGGAC AAACCTGAGG GTGGCAATAG TTAGCATGAA

1441 GGGTGAAATC GTTAAGAAGT ACACTCAGTT CAACCCTAAA

1481 ACCTATGAAG AAAGGATTAG TTTAATCCTG CAGATGTGTG

1521 TGGAAGCTGC CGCGGAAGCT GTGAAACTCA ATTGCAGAAT

1561 TCTGGGAGTA GGCATCTCCA CAGGTGGCCG CGTGAATCCC

1601 CAGGAAGGAG TTGTGCTGCA TTCAACCAAG CTGATCCAGG

1641 AATGGAACTC CGTGGACCTC AGGACACCCC TCTCCGACAC

1681 CCTGCATCTC CCCGTGTGGG TGGACAATGA CGGCAACTGT

1721 GCCGCCATGG CAGAGAGGAA GTTCGGCCAA GGAAAAGGAC

1761 AGGAGAACTT CGTGACGCTC ATCACGGGGA CAGGGATCGG

1801 TGGGGGGATC ATCCACCAGC ACGAACTGAT CCACGGCAGC

1841 TCCTTCTGCG CGGCGGAGCT CGGCCATCTC GTGGTGTCCC

1881 TGGACGGTCC TGACTGCTCC TGTGGAAGCC ATGGGTGCAT

1921 CGAAGCGTAC GCCTCTGGAA TGGCCTTGCA GAGGGAAGCA

1961 AAGAAACTCC ATGATGAGGA CCTGCTCTTG GTGGAAGGGA

2001 TGTCAGTACC AAAAGACGAA GCTGTGGGTG CCCTCCATCT

2041 CATCCAGGCT GCCAAGCTGG GCAACGTGAA GGCCCAGAGC

2081 ATCTTACGAA CAGCTGGAAC TGCTTTGGGA CTTGGGGTTG

2121 TGAACATCCT CCACACTATG AATCCTTCCC TGGTGATCCT

2161 GTCTGGAGTC CTGGCCAGTC ACTACATCCA CATCGTGAAG

2201 GACGTCATCC GCCAGCAAGC CTTGTCCTCC GTGCAGGATG

2241 TGGACGTGGT GGTCTCAGAC TTGGTGGACC CGGCCCTGCT

2281 TGGCGCAGCC AGCATGGTTC TGGACTACAC AACGCGCAGG

2321 ATCCACTAGG TCTCCCGGGA ACGGACACGG ACAGAGACTC

2361 GGGAGCTGCT TAGAGTGGAA CCATGCTCTT CTAGATCAGT

2401 GTTTCTGCGA AGGCAAATTT GGGGGGAGGG CTGCTGAGAC

2441 AGCTCAGTGG TTAAGAGCCT GCCCTGCTCC TGCCAGTCCC

2481 CAGCACCCAT GTCAGGCAGC TCAGCTGCCT GGAAGCCAAG

2521 CTCCAGGGGA CCCAATGCCT CTCTGCCGGG GGCAGCTGCA

2561 CTCAGATGTA CATACCCCTC TCCACACACA TACAAATAAA

2601 GCTTATTTTT CAAAAGGCAA AAAAAAAAA AAAAAAAAA

2641 AAAAAAAAA AAAA
```

The mutant mice were maintained in the C57BL/6J background. Animals were housed in an accredited specific pathogen-free facility in accordance with accepted guidelines. Cages were ventilated in a temperature- and light-controlled environment (22° C., 30%-70% humidity, 12-hour light/12-hour dark cycle). The mice were fed irradiated chow (Prolab 5P75 Isopro 3000; PMI Nutrition International) and sterile water ad libitum. All euthanasia was performed by $CO_2$ inhalation followed by cervical dislocation.

For Mendelian distribution studies, 4 pregnant mice at E17-E19 were euthanized, and embryos were retrieved by cesarean section and euthanized by decapitation. All mouse procedures were performed in accordance with protocol G04-3 and were approved by the Institutional Animal Care and Use Committee of the National Human Genome Research Institute.

Molecular analysis. Mouse genotyping was performed on tail genomic DNA or cDNA isolated from kidney or skeletal muscle using standard protocols. Total RNA was isolated from murine tissues using the TRIzol reagent (Invitrogen), and cDNA was prepared using the SuperScript III system (Invitrogen). PCR amplifications were performed across the M712T mutation with genomic DNA as template, using the primer set 5'- agcacttcctgagtttgatg-3' (SEQ ID NO:4) and 5'-atttgccttcgcaga-cacttga-3' (SEQ ID NO:5) (FIG. 2B) or with cDNA as template (FIG. 2C), using the primer set 5'-GCCCAGAGCATCTTACGAAC-3' (SEQ ID NO:6) and 5'-GGGTCCCCTGGAGCTTGG-3' (SEQ ID NO:7) and PuReTaq Ready-To-Go PCR beads (GE Healthcare), using standard PCR conditions. PCR fragments were digested with Nla III at 37° C. to verify the mutation status (FIGS. 2B and C). Quantitative realtime PCR was performed on RNA isolated from kidney and skeletal muscle, utilizing Assays-On-Demand (Applied Biosystems) for Gne (mm00607939), Pecam-1 (mm00476702), Col4A3 (mm01269206), and β-actin (mm00450174) on an ABI PRISM 7900 HT Sequence Detection System (Applied Biosystems).

Clinical chemistry screen. Retroorbital blood samples (100-150 ml) from weaned mice (weighing at least 15 grams) matched for sex (male) and age were obtained bimonthly after pretreatment with a topical anesthetic (0.5% tetracaine HCl; Bausch & Lomb Pharmaceuticals). Samples were allowed to clot (30 minutes at room temperature) in MicroPrep centrifuge tubes (IRIS International Inc.), after which the serum was separated by centrifugation at 1500 g for 10 minutes and stored at −80° C. until analysis. Clinical chemistry screens were performed at the Department of Laboratory Medicine at the NIH and included monitoring of creatinine, blood urea nitrogen, albumin, total protein, uric acid, alkaline phosphatase, alanine aminotransferase, aspartate aminotransferase, amylase, creatine kinase, and lactate dehydrogenase. In addition, reagent strips for protein urinalysis were used to assess proteinuria (Chemstrip 2GP; Roche Diagnostics).

Antibodies. A rabbit polyclonal antibody was custom prepared against a Gne/Mnk peptide comprising amino acids 588-607 (EAYASGMALQREAKKLHDED, SEQ ID NO:8), coupled to keyhole limpet hemocyanine, and affinity purified against the corresponding antigenic peptide (Covance). The following additional primary antibodies were commercially obtained: dystrophin (catalog no. ab15277; Abcam); α-dystroglycan (clone IIH6C4; Upstate Biotechnology); laminin-1 (catalog no. L9393; Sigma-Aldrich); podocalyxin (catalog no. PODX11-A; Alpha Diagnostic International); podocin (catalog no. P0372; Sigma-Aldrich); laminin β1 (catalog no. MAB1928; Millipore); desmin (catalog no. 1466-1; Epitomics); a-SMA (SPM332; GeneTex Inc.); PSA-NCAM (catalog no. MAB5324; Millipore); and β-actin (catalog no. AAN01; Cytoskeleton).

Mouse histology. Mouse tissues were collected, formalin fixed (10%) and paraffin embedded. Tissue sections (5 mm)

were stained with H&E following standard procedures (American Histolabs) or subjected to immunohistochemistry with a variety of primary antibodies. Formalin-fixed tissues were deparaffinized in HistoClear II (National Diagnostics) and dehydrated in a series of ethanol solutions. Antigen retrieval was performed for sections that were to be stained with antibodies against Gne/Mnk (by boiling 5 minutes in citric acid-based solution; Vector Laboratories) and against dystrophin (by boiling in 1 mM EDTA according the manufacturer's protocol; AbCam). The sections were blocked (2% BSA, 10% donkey serum, and 0.1% Triton X-100 in PBS) and incubated with primary antibodies (Gne/Mnk 1:50; laminin 1:25; dystrophin 1:50) overnight at 4° C., followed by incubation with the secondary antibody, Alexa Fluor 488-conjugated donkey anti-rabbit (1:500 in blocking solution) (Invitrogen). The sections were mounted in VECTASHIELD Mounting Medium (Vector Laboratories) and viewed and digitally imaged with a Zeiss Axiovert 200M microscope (Zeiss).

Western blotting. Mouse tissues (age P2) were extracted, homogenized in CelLytic buffer consisting of a mild detergent, bicine buffer, and 150 mM NaCl (Sigma-Aldrich) supplemented with protease inhibitors (Complete Mini; Roche Applied Science). The lysates were sonicated and cleared by centrifugation (1000 g for 10 minutes), and the resulting supernatants were assayed for protein (BCA Protein Assay; Pierce Biotechnology). For the neuraminidase enzymatic treatments (FIG. 6E), protein homogenates (25 mg) were incubated for 30 min at 37° C. with 1 mU/mg of neuraminidase (catalog no. N6514; Sigma-Aldrich). Equal amounts of protein (25-50 mg) were electrophoresed on 4%-12% Tris-Glycine gels (Novex; Invitrogen), and electroblotted onto 0.45 mm Hybond ECL nitrocellulose membranes (GE Healthcare). The membranes were blocked (10% fat-free milk) and incubated with primary antibodies followed by HRP-conjugated secondary antibodies (GE Healthcare). Results were visualized with ECL (ECL Western Blotting Detection Reagents; GE Healthcare) and exposure to CL-XPosure Film (Pierce Biotechnology). Densitometry was performed on the digital images obtained with a Kodak Image Station and software (PerkinElmer). The protein levels were normalized to those of $\beta$-actin to correct for differences in protein loading and/or transfer.

Electron microscopy. Kidney samples were fixed overnight at 4° C. in 2% glutaraldehyde in 0.1 M cacodylate buffer (pH 7.4) and washed with cacodylate buffer. After postfixation with 1% OsO4 for 2 hours and a second wash with 0.1 M cacodylate buffer, the tissues were serially dehydrated in ethanol and embedded in Eponate 12 resin (Ted Pella). Thin sections (~80 nm) were obtained using a Leica Ultracut UCT Ultramicrotome (Leica Microsystems), placed onto 400 mesh copper grids, and stained with saturated uranyl acetate in 50% methanol followed by lead citrate. The grids were viewed with a Philips 410 electron microscope (FEI Company) at 80 kV, and images were recorded on Kodak SO-163 film (Kodak).

ManNAc administration. Breeding pairs of 6-week-old $Gne^{M712T/+}$ mice were divided into 3 groups. Group I consisted of 9 $Gne^{M712T/+}$ breeding pairs, who were administered untreated sterilized tap water. Group II consisted of 1 breeding pair of $Gne^{+/+}$ mice (wild-type control) and 6 $Gne^{M712T/+}$ breeding pairs, who were administered water containing 1 mg/ml (~0.2 g/kg/day) ManNAc (Sigma-Aldrich). That dose was selected based on previous evidence of the safety of ManNAc (administered at a single dose of 0.142 g/kg/day) in a study performed in humans (21). Group III consisted of 1 $Gne^{+/+}$ breeding pair and 7 $Gne^{M712T/+}$ breeding pairs, who were administered water supplemented with 5 mg/ml (~1.0 g/kg/day) ManNAc. Water was changed twice weekly. Nursing females continued to be supplied with ManNAc. All mice were weaned from ManNAc at 21 days. Selected whole litters were euthanized at age P2, P6, and P19 for histological, genetic, biochemical, or ultrastructural analysis.

Gne enzymatic assays. Mouse kidney and skeletal muscle (quadriceps) tissues were homogenized and subjected to the Gne-epimerase enzymatic assay as previously described (11, 58). This assay was based on incubation with radiolabeled substrate (Uridine diphosphate N-acetyl glucosamine [1-$^3$H]; American Radiolabeled Chemicals Inc.) and detection of radiolabeled product ([$^3$H]ManNAc) upon separation of oligosaccharides by high-pH anion-exchange chromatography with pulsed amperometric detection (Dionex).

Statistics. Differences between data groups were evaluated for significance using the 2-tailed Student's t test of unpaired data. For Mendelian distribution analysis, a goodness-of-fit ($\chi 2$) test was performed, while for comparisons of survival between treated and untreated mice of all genotypes ($Gne^{+/+}$, $Gne^{M712T/+}$, and $Gne^{M712T/M712T}$), a 2-tailed Fisher's exact test using a 2×3 table was employed. All data are presented as the mean±SD. A P value less than 0.05 was considered statistically significant.

Results

Generation of $Gne^{M712T/M712T}$ knockinn mice. A murine targeting vector for homologous recombination in C57BL/6J embryonic stem cells was constructed to include the M712T Gne mutation (FIG. 2A). The neomycin phosphotransferase and thymidine kinase genes were introduced into the vector as positive and negative selection markers, respectively (FIG. 2A). Additional LoxP (flanking exon 12 and neo) and flippase recombinase target sites (flanking neo) were inserted for transgenic models for this condition (Nagy, A. 2000. Cre recombinase: the universal reagent for genome tailoring. *Genesis*. 26:99-109). The entire vector was sequence verified. Genotyping of the mice was performed by PCR amplification and digestion with the restriction endonuclease NlaIII (FIG. 2B). Tissues of homozygous mutant $Gne^{M712T/M712T}$ and wild-type $Gne^{+/+}$ mice showed comparable Gne RNA transcript levels by real-time quantitative PCR. Furthermore, NlaIII digestion of amplified cDNA demonstrated homozygous insertion of the M712T mutation in RNA of $Gne^{M712T/M712T}$ mice (FIG. 2C).

Figure 2E:
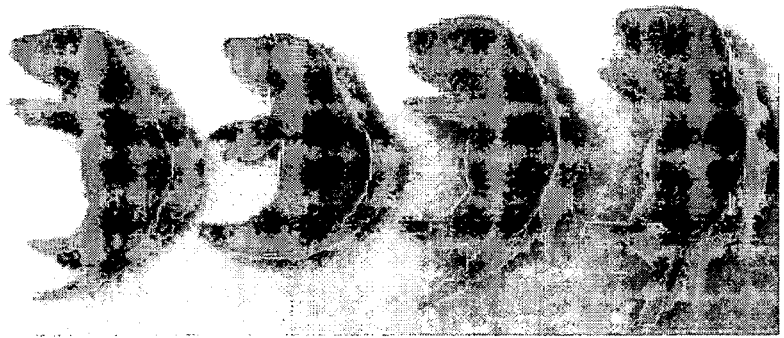

Early postnatal lethality. Initial matings of heterozygous mice ($Gne^{M712T/+}$) yielded 101 offspring from which only 1 $Gne^{M712T/M712T}$ animal survived beyond P21. The remaining $Gne^{M712T/M712T}$ offspring died at P1-P3 (FIG. 2D). However, subsequent genotyping of 35 embryos at days E17-E19 showed 26% $Gne^{+/+}$, 43% $Gne^{M712T/+}$, and 31% $Gne^{M712T/M712T}$, reflecting a Mendelian distribution, statistically confirmed by goodness-of-fit testing (l2=0.94, P=0.62) (FIG. 2D). At E17-E19, the embryos displayed normal exteriors, normal head and body sizes, and pink skin, which indicated good circulatory and respiratory function. By P2, however, $Gne^{M712T/M712T}$ mice were smaller than control littermates (FIG. 2E), weighing 70%-100% of control littermates. The $Gne^{M712T/M712T}$ mouse stomachs contained milk, although a prominent milkspot was not always visible. All $Gne^{M712T/M712T}$ mice except 1 died by P3 and had increased urinary protein. In contrast, $Gne^{M712T/+}$ mice appeared unaffected.

Histological analyses. Tissues of $Gne^{M712T/M712T}$ mice and their littermates were examined between age P2 and P3. No abnormalities were identified in skeletal muscle, heart, or liver (data not shown). Moreover, immunohistochemical staining with antibodies against laminin and dystrophin failed to show differences between muscle sections of $Gne^{M712T/M712T}$ mice and their wild-type littermates.

Figure 3A:
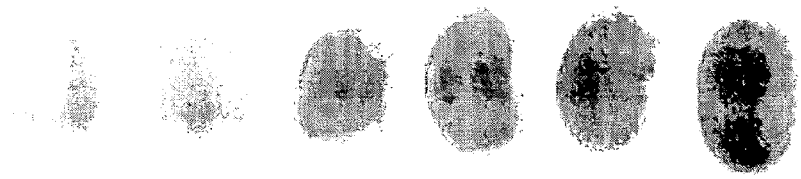
FIG. 3A-E provides results of histological kidney analyses.
Figure 3B:
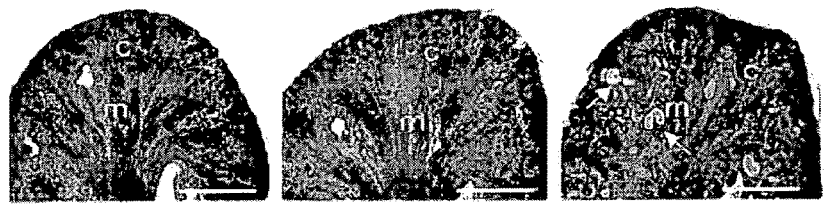
Figure 3C:
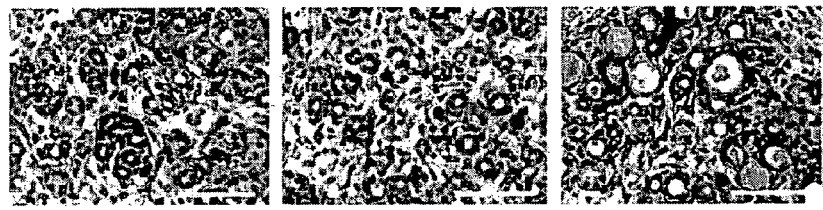
Figure 3D:
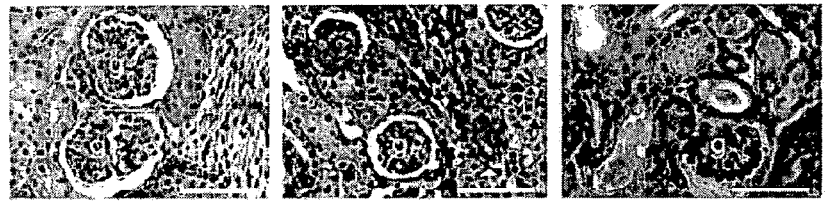
Figure 3E:
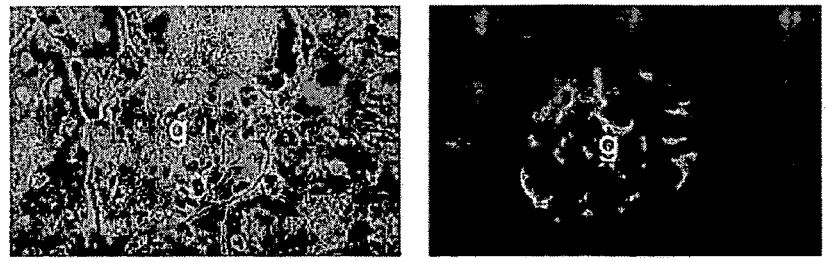

At age P2, kidneys of $Gne^{M712T/M712T}$ mice showed petechial hemorrhages by gross examination, but were normal in size and shape compared with kidneys of $Gne^{+/+}$ and $Gne^{M712T/+}$ littermates (FIG. 3A). Histological analyses revealed cystic tubular dilatation (FIG. 3B). High-magnification views of $Gne^{M712T/M712T}$ kidneys showed red blood cell infiltrates in the proximal and distal convoluted tubules and the collecting ducts (FIG. 3C). The glomeruli of $Gne^{M712T/M712T}$ mice contained red blood cell infiltrates in Bowman space (FIG. 3D). Of 100 glomeruli scored in each group, 64%±6% were affected in $Gne^{M712T/M712T}$ mice (n=4) compared with 2%±1% in $Gne^{M712T/+}$ mice (n=3) and 4%±4.5% in $Gne^{+/+}$ mice (n=4). Immunohistochemical analysis demonstrated localization of Gne/Mnk antibodies to kidney glomeruli (FIG. 3E). Examination of $Gne^{M712T/M712T}$ kidneys at E18 showed no histological differences compared with wild-type or heterozygous littermates (data not shown).

Figure 4A:
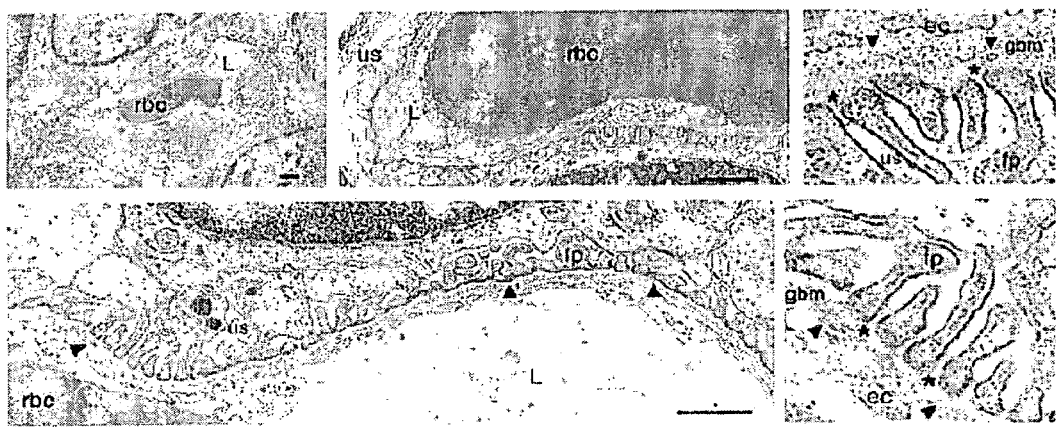
FIG. 4A-D shows transmission electron microscope images of mouse kidney sections.
Figure 4B:

Ultrastructural analyses of the glomeruli at age P2 revealed that, compared with the slender, well-shaped glomerular foot processes of wild-type mice (FIG. 4A), the podocyte foot process membranes of $Gne^{M712T/M712T}$ mice were flattened and largely fused, with only a few wide foot processes remaining (FIG. 4B). Filtration slits were reduced in number and showed formation of tight junction-like structures (FIG. 4B). In addition, the GBM showed segmental splitting of the lamina densa (FIG. 4B). The size and shape of endothelial cells lining the basement membrane, as well as glomerular mesangial cells, appeared ultrastructurally intact.

Figure 6A:
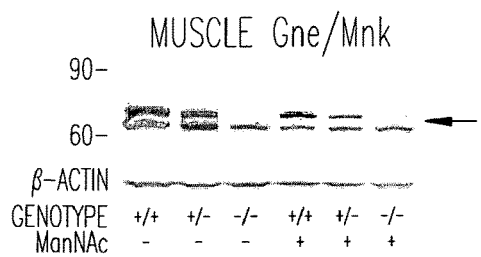
FIG. 6A-E shows immunoblots of muscle, kidney, and brain extracts of knockin mice. Immunoblots of muscle (FIG. 6A) and kidney (FIG. 6B) extracts exhibited decreased Gne/Mnk protein expression (upper band, arrows, 79 kDa) in homozygous mutant $Gne^{M712T/M712T}$ (−/−) mice compared with heterozygous (+/−) and wild-type (+/+) littermates (normalized to β-actin). Gne/Mnk protein expression increased upon ManNAc feeding in $Gne^{M712T/M712T}$ (−/−) tissues when compared with untreated tissues.
Figure 6B:
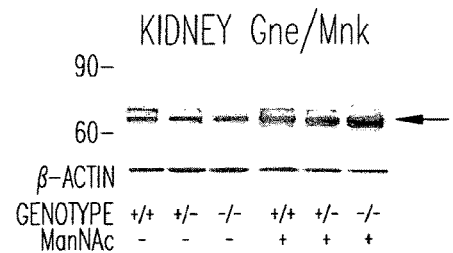
Figure 6C:
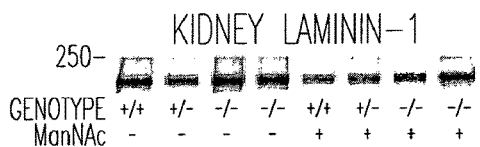

To support these ultrastructural findings, additional analyses were performed using markers for specific glomerular compartments. The podocyte-specific markers podocin and podocalyxin (Pavestadt et al., *Physiol. Rev.* 83: 253-307 (2003); Dekan et al. *Proc. Natl. Acad. Sci. USA* 88: 5398-5402 (1991)) were tested by immunoblotting kidney extracts of all genotypes. While podocin showed no difference in expression across all genotypes (at age P1) (data not shown), podocalyxin, the major sialoglycoprotein of the podocyte apical membrane (Pavestadt et al.; Dekan et al.), demonstrated dramatically decreased sialylation (FIG. 6E, upper gel). Expression levels of GBM markers laminin-1 (FIG. 6C) and laminin β1 (data not shown) were unchanged in $Gne^{M712T/M712T}$ kidneys, as were RNA levels of collagen type IV α3 (Col4A3), an integral GBM component. Immunoblotting with desmin and vascular SMA, antibodies to mesangial cell markers (Ichimura et al. *J. Histochem. Cytochem.* 54: 1291-1301 (2006)), showed similar expression levels across all genotypes. In addition, real-time quantitative PCR analysis of the endothelial cell marker CD31/Pecam-1 revealed no difference in RNA expression levels across genotypes at P1. Serum metabolite studies on the only $Gne^{M712T/M712T}$ mouse that survived past weaning demonstrated elevated blood urea nitrogen levels (39±10 mg/dl in $Gne^{M712T/M712T}$ mouse versus 21±2 mg/dl in $Gne^{+/+}$ mice) and increased urinary protein (>500 mg/dl protein), which indicated renal disease. All other serum metabolites tested, including creatinine and creatine kinase, were within the normal ranges. This male $Gne^{M712T/M712T}$ survivor was euthanized at age 8.5 months. Histologic analysis revealed no structural abnormalities in the forelimb or hindlimb. However, severe bilateral hydronephrosis and changes consistent with glomerulopathy were found in the kidneys.

Figure 4C:
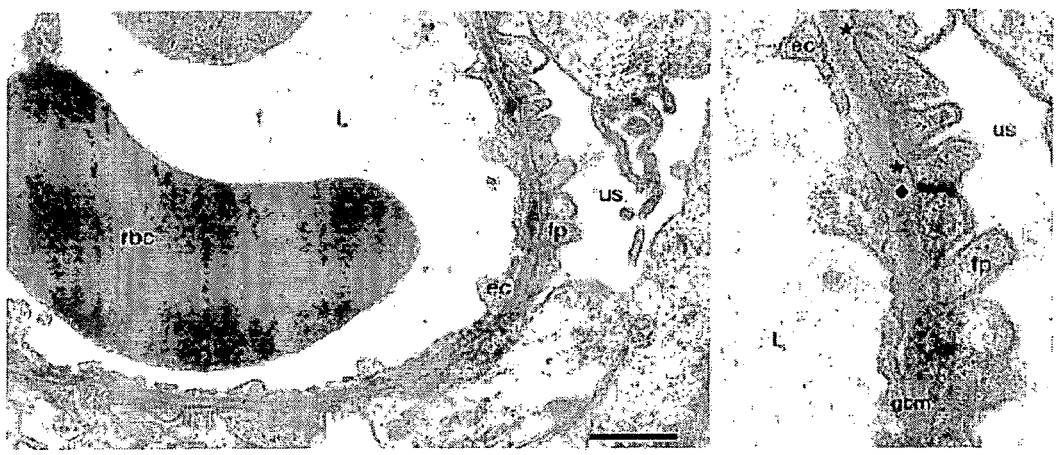
Figure 4D:
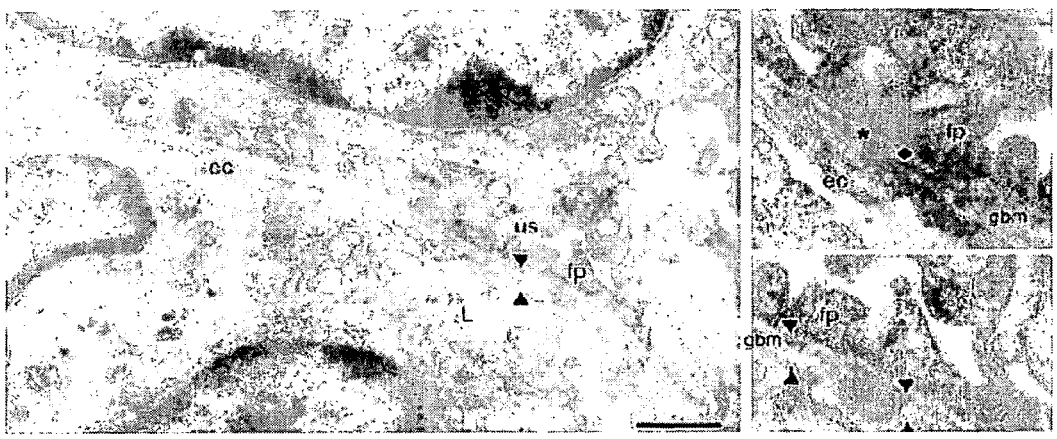

Rescue by ManNAc feeding. ManNAc, added to the drinking water at a concentration of 1 mg/ml (~0.2 g/kg/day) during matings of $Gne^{M712T/+}$ mice, yielded no surviving homozygous $Gne^{M712T/M712T}$ mice beyond age P3 from among 51 offspring (FIG. 5A). However, at 5 mg ManNAc/ml (~1.0 g/kg/day), among 102 total newborns, 12 $Gne^{M712T/M712T}$ pups survived beyond P3, a significantly greater number compared with the 1 survivor in the untreated group (2-tailed Fisher's exact test, P=0.01) (FIG. 5A). ManNAc at the administered dose (~1.0 g/kg/d) was well tolerated by the mice, and no side effects were attributed to the treatment throughout the study. Surviving $Gne^{M712T/M712T}$ mice remained smaller than their wild-type littermates, weighing 70%-100%. At age P6, ManNAc treated $Gne^{M712T/M712T}$ mice exhibited no abnormalities in liver, heart, or skeletal muscle tissues (data not shown). Their kidneys demonstrated significant histological improvement (FIG. 5B-D) compared with $Gne^{M712T/M712T}$ mice examined at age P2 (FIG. 3B-D). Upon ManNAc treatment, there were fewer cystic tubular dilatations in the cortex and medulla (FIG. 5B) and reduced red blood cell infiltrates in the tubules and the Bowman space (FIGS. 5C and D). Ultrastructural analysis at age P19 showed less fusion and flattening of the podocyte foot processes including a greater number of open slit diaphragms and an improvement in the "finger shaping" of the foot processes (FIGS. 4C and D). The overall integrity of the GBM was also significantly improved, although occasional segmental splitting of the lamina densa was still apparent (FIGS. 4C and D).

The nursing females continued to receive ManNAc treatment until the pups were weaned (P21). Of the twelve $Gne^{M712T/M712T}$ mice that survived past P3, nine died between P6 and P12. One $Gne^{M712T/M712T}$ mouse was sacrificed at age P19 for ultrastructural analysis. Two $Gne^{M712T/M712T}$ mice survived past P21, when ManNAc supplementation was ceased. These two mice continued to grow without receiving additional ManNAc but remained smaller than their littermates (FIG. 5E). At 3.5 months of age, one $Gne^{M712T/M712T}$ survivor was sacrificed because of hydrocephalus and malocclusion. Similar events occurred in some untreated mice at different ages and were found not to be related to treatment or the disease. Skeletal muscle histology of this mouse revealed no structural or inflammatory abnormalities, but the kidneys showed mild red blood cell infiltrations in the urinary space and the tubules. The one surviving $Gne^{M712T/M712T}$ mouse is currently 6 months old and has no obvious myopathic features.

Biochemical analyses following ManNAc feeding. Gne enzymatic activity was measured in muscle and kidney at age P2. Skeletal muscle of $Gne^{M712T/M712T}$ mice showed 19.4%±7.5 of the Gne activity of the Gne+/+ mice (n=4, P=0.02) (FIG. 5F). Similar decreases in Gne activities were measured in $Gne^{M712T/M712T}$ kidney extracts (10% of mean $Gne^{+/+}$ kidney epimerase activities). Upon ManNAc treatment, Gne activities in Gne $^{+/+}$ muscle (n=3) increased to 114% (±19.7) (P=0.2), while $Gne^{M712T/M712T}$ muscle activity (n=7) increased from 19.4% (±7.5) to 31% (±8.4) of untreated $Gne^{+/+}$ mean values of muscle Gne activity (P=0.05) (FIG. 5F). Immunoblots of muscle and kidney extracts labeled with anti-Gne/Mnk antibodies demonstrated 38.5% (±27, n=4) Gne/Mnk protein in $Gne^{M712T/M712T}$ muscle and 32.1% (±7, n=3) in $Gne^{M712T/M712T}$ kidney tissues when compared with $Gne^{+/+}$ littermates. This improved upon ManNAc treatment of $Gne^{M712T/M712T}$ mice to 68.8% (±20, n=4) in muscle and to 62.2% (±9.7, n=4) in kidney tissues (P=0.12 and P=0.006 for muscle and kidney values respectively, relative to β-actin) (FIGS. 6A and B). Immunoblots stained with antibodies against laminin-1, an integral component of the GBM (25-27), showed similar patterns across genotypes before and after treatment (FIG. 6C).

The degree of sialylation of two heavily sialylated marker proteins, PSA-NCAM and podocalyxin was evaluated. PSA-NCAM is a major sialoprotein expressed in neonatal brains (Galuska et al., *J. Biol. Chem.* 281: 31605-15 (2006)), where its expression is regulated by the intracellular concentration of sialic acid (Bork et al., *FEBS letters* 579: 5079-83 (2005)).

Figure 6D:
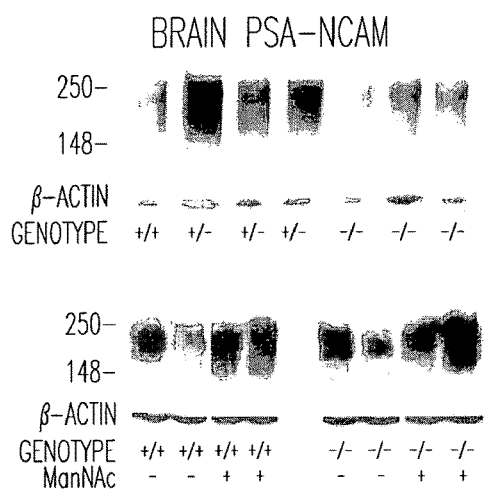
Figure 6E:
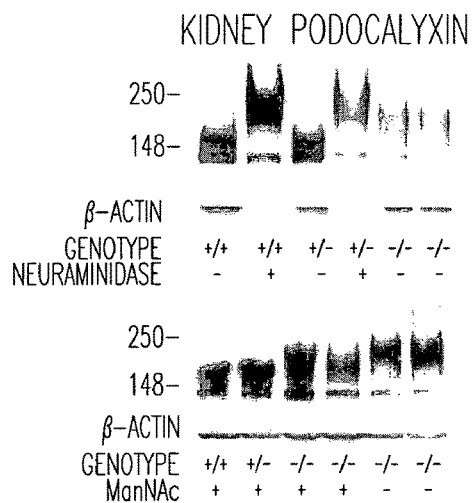

FIG. 6 shows that the expression of PSA-NCAM varied within and between genotypes, yet $Gne^{M712T/M712T}$ brains at P2 showed up to 80% decreased PSA-NCAM expression compared with that in Gne+/+ mice (FIG. 6D, upper gel). A 2%-28% increase compared with $Gne^{M712T/M712T}$ untreated mice following ManNAc treatment was observed (n=14 before treatment and n=10 after treatment, P=0.08) (FIG. 6D, lower gel). The expression of PSA-NCAM in normal muscle and kidney at P2 was low, and no change upon treatment in these tissues could be confirmed (data not shown). In addition, the significantly decreased sialylation status of podocalyxin in untreated $Gne^{M712T/M712T}$ kidneys (FIG. 6E, lower gel) markedly improved upon ManNAc treatment (FIG. 6E, upper gel).

Therefore, this Example describes a knockin mice harboring a M712T Gne/Mnk mutation that was generated by the inventors. Homozygous mutant ($Gne^{M712T/M721T}$) mice did not survive beyond P3 unless treated with ManNAc. At P2, significantly decreased Gne-epimerase activity was observed in $Gne^{M712T/M712T}$ muscle, but no myopathic features were apparent. Rather, homozygous mutant mice had glomerular hematuria, proteinuria, and podocytopathy. Renal findings included segmental splitting of the glomerular basement membrane, effacement of podocyte foot processes, and reduced sialylation of the major podocyte sialoprotein, podocalyxin. ManNAc administration led to survival beyond P3 in 43% of the $Gne^{M712T/M712T}$ pups. Survivors exhibited improved renal histology, increased sialylation of podocalyxin, and increased Gne/Mnk protein expression and Gne-epimerase activities. These findings indicate that ManNAc may be a useful treatment not only for HIBM but also for renal disorders involving proteinuria and hematuria due to podocytopathy and/or segmental splitting of the glomerular basement membrane.

EXAMPLE 2

Administration to Humans—Clinical Studies

Patients will be recruited from the Iranian Jewish community, from groups of patients known to have HIBM, and from individuals previously enrolled in protocol 76-HG-0238, "Diagnosis and Treatment of Patients with Inborn Errors of Metabolism," protocol 01-N-0149, "Diagnostic Evaluation of Patients with Neuromuscular Diseases," or protocol 05-HG-0236, "Pilot Study of the Use of Intravenous Immune Globulin in Hereditary Inclusion Body Myopathy." Patients will also be recruited from the patient organization ARMS (Advancement of Research for Myopathies).

Materials

ManNAc for human use will be purchased from Meropharm AG (Eugensbergstrasse 14, 8268 Salenstein, Switzerland). It will be prepared as 500 mg enteric coated capsules by the Clinical Center Pharmaceutical Development Service (PDS), who will also prepare a placebo containing mannose. ManNAc or placebo will be taken orally in four divided doses, thirty minutes before meals. ManNAc and placebo capsules will be delivered monthly for each study patient and stored in the refrigerator. All bottles will be labeled in the same way and there will be no apparent difference between ManNAc and placebo capsules in color, shape or taste of the coating.

Procedures

Baseline evaluations will include a detailed determination of the extent of neuromuscular disease prior to treatment. The history and physical examination will include elucidation of the family pedigree, neurological status, and muscle strength. Baseline laboratory tests will also include a routine urinalysis. Women will receive a pregnancy test. Blood will be drawn for CBC and differential, platelets, erythrocyte sedimentation rate, electrolytes, calcium, phosphorus, liver enzymes, lipid panel, alkaline phosphatase, prothrombin time, partial thromboplastin time, creatine phosphokinase, HbA1C, fasting glucose and insulin, free T4 and TSH, FSH, LH, testosterone and estradiol. A purple top tube will be obtained for DNA/RNA extraction, a yellow top for lymphoblast transformation and separate yellow and brown tops for platelet and white cell pellets. The DNA/RNA will be used to perform or confirm mutational analysis of the GNE gene. The cells will be used for basic research studies, including assessment of the sialylation status of glycoproteins. Blood and urine will also be obtained for determination of serum and urine ManNAc and free sialic acid levels. In addition to spot urine tests, a 24-hour urine collection will be analyzed for creatinine clearance, protein, albumin, protein electrophoresis, β2-microglobulin, and amino acid analysis. Baseline blood tests and their volumes are as follows:

|  | # Drawn | ml/Test | Total Volume (ml) |
|---|---|---|---|
| CBC, ESR, platelets | 1 | 3.0 | 3.0 |
| Chem 20 panel, CPK, & fasting glucose and lipid panel | 1 | 3.5 | 3.5 |
| PT, PTT | 1 | 4.5 | 4.5 |
| HbA1C, Insulin | 1 | 3.5 | 3.5 |
| Free T4/TSH | 1 | 3.5 | 3.5 |
| FSH, LH, Test,, Estradiol | 1 | 5.0 | 5.0 |
| Lymphoblasts | 1 | 5.0 | 5.0 |
| Platelet pellet | 1 | 5.0 | 5.0 |
| Leucocyte pellet/amino acids | 1 | 5.0 | 5.0 |
| DNA/RNA | 1 | 8.0 | 8.0 |
| Serum ManNAc, SA | 2 | 4.0 | 8.0 |
| Total |  |  | 54.0 |

In addition, up to 30 ml of blood may be removed for research purposes. However, under no circumstances will more than 450 ml of blood be withdrawn during any 6-week period. Patients' saliva will also be collected. In addition, a radiograph of the chest, an echocardiogram and an electrocardiogram and a 24 h ambulatory ECG will be obtained.

The primary outcome parameter will be a change in quadriceps muscle strength, as well as secondary outcome parameters. Maximal voluntary isometric contraction (MVIC) assessment will be used to measure changes in the strength of the quadriceps muscles and 10 other muscle groups. MVIC assessment has proven reliable and sensitive to small changes in the evaluation of myopathy syndromes and their response to treatment. For MVIC, the quantitative muscle assessment (QMA) system-version 42+XL will be used. This system consists of an adjustable strap, attaching the limb to an interface SM250 force transducer. Patients will be tested on an adjustable examining table (Neurological Plinth Model), enclosed in a stable aluminum frame that anchors the transducer. The generated force is transmitted to an electronic strain-gauge tensiometer and is then recorded and amplified by the computer-assisted analog/digital data collection system (S/N A98C36). The measured force is expressed as the amount of kilograms (kg) that the patient exerts against the strain gauge.

Measurements will be performed by standardized testing modified from the protocol of Andres et al. (*Neurology* 36, 937-941 (1986)). The following muscle groups will be tested in a fixed order: right shoulder abductors, right elbow flexors, right elbow extensors, left shoulder abductors, left elbow flexors, left elbow extensors, right ankle dorsiflexors, left ankle dorsiflexors, right knee flexors and left knee flexors, left knee extensors, right knee extensors. All muscle groups will be tested twice with a minimum of 30 seconds rest between the trials. If measurements differ by more than 15% a third test will be performed. The average of the two more similar measurements will be used as the score for that particular test. The patients will be informed about the test purpose and procedure before the start of the study and verbal encouragement will be given during the tests.

Patients will also perform a 6-minute walk test, a timed up-and-go test, measures of pinch and grip strength, and the forward/functional reach test.

Skeletal muscle strength will also be measured by physical examination. The 10-point manual muscle testing (MMT-28) scale (Jain et al. *Phys Occup Ther Pediatr* 26, 5-17 (2006)), in which 0 is the lowest and 10 the highest score, will be used for grading of the response. The MMT will be performed by a physical therapist who will remain blinded and will include physical examination of the following 13 muscle groups on each side: deltoid, biceps brachii, triceps brachii, brachioradialis, wrist extensors, wrist flexors, iliopsoas, gluteus maximus, quadriceps femoris, hamstrings, and foot extensors and flexors.

Pulmonary function tests will be performed as a measure of the strength of the muscles of the thoracic cage. Spirometry, with or without bronchodilators, will be employed to assess forced vital capacity (FVC) and forced expiratory volume in 1 sec (FEV1). In addition, maximal inspiratory and expiratory pressures (MIP and MEP) and maximum voluntary ventilation (MVV) will be recorded using standard techniques. The best result of three trials will be recorded. Lung volumes and diffusion capacity will be assessed at baseline and repeated if clinically indicated.

Self-report assessments that capture global clinical improvement will include the Human Activity Profile (Fix, A. J., and Daughton, D. M. (1998) *Human Activity Profile Professional Manual*. Psychological Assessment Resources Inc.) and the SF-36v2 quality of life questionnaires (Ware et al. *Med Care* 30, 473-483 (1992)), to be completed by the patients at the beginning and end of each crossover period.

Figure 7:
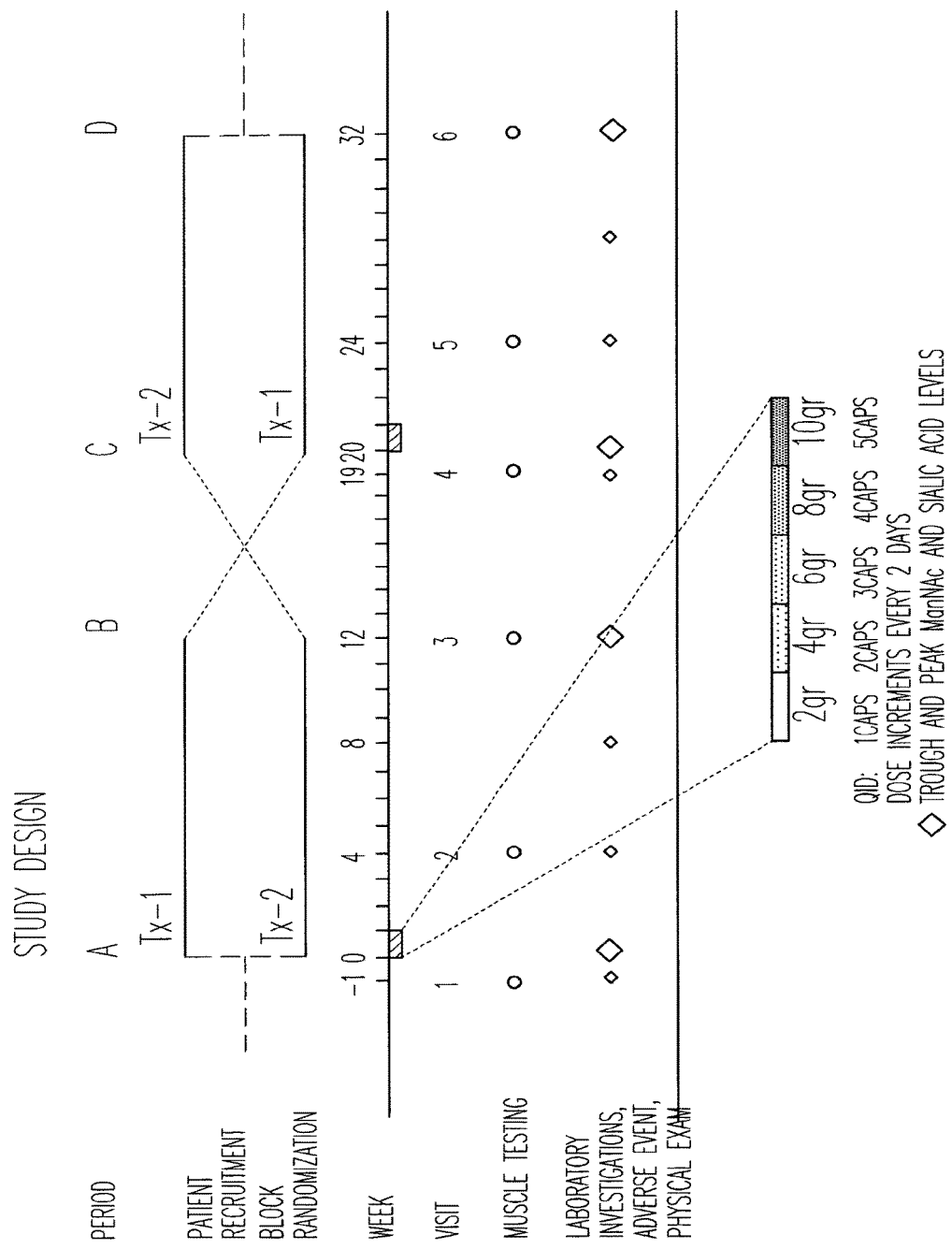
FIG. 7 schematically illustrates a timeline for administration of N-acetyl mannosamine during a clinical trial of human patients.

After baseline testing, patients will be randomized and ManNAc/placebo treatment will begin. The dose will be increased gradually every two days, as follows: 1 capsule (500 mg) ManNAc/placebo four times a day (q.i.d.) for two days, followed by 1 capsule q.i.d. incremental increase every two days until the full dose of ~10 g, or 5 capsules q.i.d. is reached (FIG. 7). Serum trough and peak levels (at 30 min, 1, 2 and 4 hours post administration) of ManNAc, as well as glucose will be obtained after the first administration of ManNAc on the second day of a certain dose during the incremental dosing week. At the end of each treatment period trough and peak (1 hour) levels will be obtained after each dose over 24 hours.

Once the full dose of 10 g/day is reached, a repeat ECG or 24 h ambulatory ECG monitoring (Holter), spot urinalysis and the following blood tests will be performed for safety reasons:

|  | # Drawn | ml/Test | Total Volume (ml) |
| --- | --- | --- | --- |
| CBC, ESR, platelets | 1 | 3.0 | 3.0 |
| Chem 20 panel, CPK, & fasting glucose, lipids | 1 | 3.5 | 3.5 |
| PT, PTT | 1 | 4.5 | 4.5 |
|  | Total |  | 11.0 |

The patients will be discharged home on the 10 g/day dose, to return for follow-up admissions at one month and 3 months. This schedule will be repeated for the second crossover period after a 6-week washout period.

Follow-Up Studies

Follow-up evaluations will occur at the one-month time point for each crossover period, and at the end of each crossover period. They will consist of a one-week admission involving repeat 24-hour urine studies and the following blood tests:

|  | # Drawn | ml/Test | Total Volume (ml) |
| --- | --- | --- | --- |
| CBC, ESR, platelets | 1 | 3.0 | 3.0 |
| Chem 20 panel, CPK, & fasting glucose, lipids | 1 | 3.5 | 3.5 |
| PT, PTT | 1 | 4.5 | 4.5 |
| HbA1C, Insulin | 1 | 3.5 | 3.5 |
| Free T4/TSH | 1 | 3.5 | 3.5 |
| FSH, LH, Test., Estradiol | 1 | 5.0 | 5.0 |
| Platelet pellet | 1 | 5.0 | 5.0 |
| Leucocyte pellet/amino acids | 1 | 5.0 | 5.0 |
| Serum ManNAc, SA | 1 | 4.0 | 8.0 |
|  | Total |  | 37.0 |

Follow-up procedures and consultations will involve repeat ECG or 24 h ambulatory ECG monitoring (Holter) and echocardiogram, muscle quantitative strength assessments, functional muscle studies, PFTs, and functional and quality of life questionnaires.

To monitor treatment at home, patients will be asked to complete a weekly diary (available both electronically and in hard-copy) in order to record missed doses, GI upset or other side-effects, and observed improvements.

Statistical Considerations

Patients will be randomized using a permuted block size to either ManNAc or placebo (1:1) in a double-blind fashion (block randomization by the National Institutes of Health Clinical Center Pharmacy) to ensure balanced assignment to the two groups of patients with respect to disease duration and severity. There will be two 3-month crossover periods separated by at least 6-week washout period. Each patient will serve as his/her own control. The randomization code will not be broken until completion of the study and analysis of the results.

The primary clinical outcome parameter will be change in quadriceps muscle strength, assessed by maximum voluntary isometric contraction testing (MVIC) that will be performed at baseline, 1 month after initiation of treatment and at the end of each treatment period. Change in strength (kg) will be expressed as % of baseline. Paired t-tests and the Wilcoxon matched pairs signed rank test will be employed for the analysis.

Secondary outcome parameters will include functional muscle testing using the 6-minute walk test, functional reach, timed up-and-go, grip strength and pulmonary function tests. Lastly, each patient's global assessment of improvement will be based on the Human Activity Profile (ALSFRS) and SF-36 quality of life questionnaires, and myo-specific self-assessment scores will be obtained for depression, fatigue, and function.

The estimated sample size is based upon different pieces of data, including the inventors' experience with four HIBM patients whose muscle strength was quantified before and after a month of intravenous immune globulin treatments as a source of sialic acid (Sparks, S., et al. *BMC Neurol* 7, 3 (2007)). There was a highly significant correlation between the change in left quadriceps strength and the change in right quadriceps strength. Therefore, the mean of the two sides as the primary outcome parameter will be used in larger clinical studies. Next, a change of 0% in patients before and after the 3-month placebo treatment will be assumed, based upon the fact that significant progression of muscle weakness takes years to occur. An estimated 10% standard deviation is expected for the baseline and post-treatment measurements, and a 10% standard deviation for the mean difference, which would be 0 for placebo treatment. The coefficient of variation for the MIVC method of quantitative muscle strength testing in the literature is 6-15%. Andres, P. L., et al. *Neurology* 36, 937-941 (1986); Colombo, R., et al. *Med Eng Phys* 22, 167-174 (2000); A comparison of muscle strength testing techniques in amyotrophic lateral sclerosis. *Neurology* 61, 1503-1507 (2003); Mayhew, J. E., et al. *Muscle Nerve* 35, 36-42 (2007); Symons, T. B., et al. *J Gerontol A Biol Sci Med Sci* 60, 114-11 (2005).

A 20% improvement in quadriceps muscle strength is predicted, based upon several considerations. First, this would be a clinically significant improvement, and a smaller benefit might not detectable or significant. Second, in intravenous immune globulin (IVIG) study conducted by the inventors, the mean (SD) improvement in strength for the 8 quadriceps of 4 treated patients was 39±50%, so that a 20% improvement is conservative. Third, assuming complete absorption and conversion of ManNAc to sialic acid, 1000 times the sialic acid is delivered compared to the amount of IVIG delivered in the previous study. A standard deviation of muscle strength change under ManNAc treatment is estimated to be 26%, because the SD/mean ratio of 26/20 is the same as the SD/mean ratio of 50/39 observed in the IVIG study.

Under these conditions, a 20% difference will be detected using 18 patients with a power of 0.90 and p=0.05. Twenty patients will be treated, with the expectation that two to drop out. Up to 30 patients will hopefully be enrolled to obtain 20 who meet eligibility requirements.

This power analysis is conservative, since one-month data could strengthen the effect, a 20% improvement may be an underestimate, and the relative SD for % improvement of 18 patients is likely to be less than that of the 4 patients upon whom we based the estimate. Changes in secondary outcome parameters will be analyzed using a one-tailed t-test and p=0.025.

Oral ManNAc supplementation could provide HIBM patients with transient improvements in muscle strength and feelings of well-being. It may also prevent deterioration in their clinical course and be useful in treating the muscle weakness of HIBM. The clinical trial will also establish the safety and tolerability of ManNAc for human use. This may serve as a basis for other potential therapeutic applications of ManNAc, such as the potential benefit for podocytopathies and glomerular basemement membrane diseases suggested from our animal studies.

REFERENCES

1. Argov, Z., et al. (2003) Hereditary inclusion body myopathy: the Middle Eastern genetic cluster. *Neurology* 60, 1519-1523
2. Eisenberg, I., et al. (2001) The UDP-N-acetylglucosamine 2-epimerase/N-acetylmannosamine kinase gene is mutated in recessive hereditary inclusion body myopathy. *Nat Genet* 29, 83-87
3. Griggs, R. C., et al. (1995) Inclusion body myositis and myopathies. *Ann Neurol* 38, 705-713
4. Askanas, V., and Engel, W. K. (1998) Sporadic inclusion-body myositis and hereditary inclusion-body myopathies: current concepts of diagnosis and pathogenesis. *Curr Opin Rheumatol* 10, 530-542
5. Nishino, I., et al. (2005) Molecular pathomechanism of distal myopathy with rimmed vacuoles. *Acta Myol* 24, 80-83
6. Askanas, V., et al. (1993) beta-Amyloid precursor epitopes in muscle fibers of inclusion body myositis. *Ann Neurol* 34, 551-560
7. Argov, Z., et al. (1998) Genetics of inclusion body myopathies. *Curr Opin Rheumatol* 10, 543-547
8. Tanner, M. E. (2005) The enzymes of sialic acid biosynthesis. *Bioorg Chem* 33, 216-228
9. Stasche, R., et al. (1997) A bifunctional enzyme catalyzes the first two steps in N-acetylneuraminic acid biosynthesis of rat liver. Molecular cloning and functional expression of UDP-N-acetyl-glucosamine 2-epimerase/N-acetyl-mannosamine kinase. *J Biol Chem* 272, 24319-24324
10. Hinderlich, S., et al. (1997) A bifunctional enzyme catalyzes the first two steps in N-acetylneuraminic acid biosynthesis of rat liver. Purification and characterization of UDP-N-acetylglucosamine 2-epimerase/N-acetylmannosamine kinase. *J Biol Chem* 272, 24313-24318
11. Jacobs, C. L., et al. (2001) Substrate specificity of the sialic acid biosynthetic pathway. *Biochemistry* 40, 12864-12874
12. Nishino, I., et al. (2002) Distal myopathy with rimmed vacuoles is allelic to hereditary inclusion body myopathy. *Neurology* 59, 1689-1693
13. Kayashima, T., et al. (2002) Nonaka myopathy is caused by mutations in the UDP-N-acetylglucosamine-2-epimerase/N-acetylmannosamine kinase gene (GNE). *J Hum Genet* 47, 77-79
14. Hinderlich, S., et al. (2003) Distal myopathy with rimmed vacuoles is allelic to hereditary inclusion body myopathy. *Neurology* 61, 145; author reply 145
15. Broccolini, A., et al. (2004) Novel GNE mutations in Italian families with autosomal recessive hereditary inclusion-body myopathy. *Hum Mutat* 23, 632
16. Eisenberg, I., et al. (2003) Mutations spectrum of GNE in hereditary inclusion body myopathy sparing the quadriceps. *Hum Mutat* 21, 99
17. Tomimitsu, H., et al. (2002) Distal myopathy with rimmed vacuoles: novel mutations in the GNE gene. *Neurology* 59, 451-454
18. Darvish, D., et al. (2002) Four novel mutations associated with autosomal recessive inclusion body myopathy (MIM: 600737). *Mol Genet Metab* 77, 252-256

19. Sparks, S. E., et al. (2005) Use of a cell-free system to determine UDP-N-acetylglucosamine 2-epimerase and N-acetylmannosamine kinase activities in human hereditary inclusion body myopathy. *Glycobiology* 15, 1102-1110
20. Penner, J., et al. (2006) Influence of UDP-GlcNAc 2-epimerase/ManNAc kinase mutant proteins on hereditary inclusion body myopathy. *Biochemistry* 45, 2968-2977
21. Varki, A. (1997) Sialic acids as ligands in recognition phenomena. *Faseb J* 11, 248-255
22. Varki, A., and Diaz, S. (1984) The release and purification of sialic acids from glycoconjugates: methods to minimize the loss and migration of O-acetyl groups. *Anal Biochem* 137, 236-247
23. Schauer, R. (2000) Achievements and challenges of sialic acid research. *Glycoconj J* 17, 485-499
24. Kelm, S., and Schauer, R. (1997) Sialic acids in molecular and cellular interactions. *Int Rev Cytol* 175, 137-240
25. Keppler, O. T., et al. (1999) UDP-GlcNAc 2-epimerase: a regulator of cell surface sialylation. *Science* 284, 1372-1376
26. Schwarzkopf, M., et al. (2002) Sialylation is essential for early development in mice. *Proc Natl Acad Sci USA* 99, 5267-5270
27. Michele, D. E., et al. (2002) Post-translational disruption of dystroglycan-ligand interactions in congenital muscular dystrophies. *Nature* 418, 417-422
28. Michele, D. E., and Campbell, K. P. (2003) Dystrophin-glycoprotein complex: post-translational processing and dystroglycan function. *J Biol Chem* 278, 15457-15460
29. Martin, P. T., and Freeze, H. H. (2003) Glycobiology of neuromuscular disorders. *Glycobiology* 13, 67R-75R
30. Martin-Rendon, E., and Blake, D. J. (2003) Protein glycosylation in disease: new insights into the congenital muscular dystrophies. *Trends Pharmacol Sci* 24, 178-183
31. Huizing, M., et al. (2004) Hypoglycosylation of alpha-dystroglycan in patients with hereditary IBM due to GNE mutations. *Mol Genet Metab* 81, 196-202
32. Savelkoul, P. J., et al. (2006) Normal sialylation of serum N-linked and O-GalNAc-linked glycans in hereditary inclusion-body myopathy. *Mol Genet Metab* 88, 389-390
33. Sparks, S., et al. (2007) Intravenous immune globulin in hereditary inclusion body myopathy: a pilot study. *BMC Neurol* 7, 3
34. Broccolini, A., et al. (2005) alpha-Dystroglycan does not play a major pathogenic role in autosomal recessive hereditary inclusion-body myopathy. *Neuromuscul Disord* 15, 177-184
35. Ricci, E., et al. (2006) NCAM is hyposialylated in hereditary inclusion body myopathy due to GNE mutations. *Neurology* 66, 755-758
36. Salama, I., et al. (2005) No overall hyposialylation in hereditary inclusion body myopathy myoblasts carrying the homozygous M712T GNE mutation. *Biochem Biophys Res Commun* 328, 221-226
37. Tajima, Y., et al. (2005) Distal myopathy with rimmed vacuoles: impaired O-glycan formation in muscular glycoproteins. *Am J Pathol* 166, 1121-1130
38. Hinderlich, S., et al. (2001) Biosynthesis of N-acetylneuraminic acid in cells lacking UDP-N-acetylglucosamine 2-epimerase/N-acetylmannosamine kinase. *Biol Chem* 382, 291-297
39. Maru, I., et al. (1996) Molecular cloning and identification of N-acyl-D-glucosamine 2-epimerase from porcine kidney as a renin-binding protein. *J Biol Chem* 271, 16294-16299
40. Noguchi, S., et al. (2004) Reduction of UDP-N-acetylglucosamine 2-epimerase/N-acetylmannosamine kinase activity and sialylation in distal myopathy with rimmed vacuoles. *J Biol Chem* 279, 11402-11407
41. Keppler, O. T., et al. (1999) Differential sialylation of cell surface glycoconjugates in a human B lymphoma cell line regulates susceptibility for CD95 (APO-1/Fas)-mediated apoptosis and for infection by a lymphotropic virus. *Glycobiology* 9, 557-569
42. Thomas, G. H., et al. (1985) Accumulation of N-acetylneuraminic acid (sialic acid) in human fibroblasts cultured in the presence of N-acetylmannosamine. *Biochim Biophys Acta* 846, 37-43
43. Bork, K., et al. (2005) The intracellular concentration of sialic acid regulates the polysialylation of the neural cell adhesion molecule. *FEBS Lett* 579, 5079-5083
44. Gu, X., and Wang, D. I. (1998) Improvement of interferon-gamma sialylation in Chinese hamster ovary cell culture by feeding of N-acetylmannosamine. *Biotechnol Bioeng* 58, 642-648
45. Sampathkumar, S. G., et al. (2006) Metabolic installation of thiols into sialic acid modulates adhesion and stem cell biology. *Nat Chem Biol* 2, 149-152
46. Amir, S. M., et al. (1966) Administration of N-acetyl-D-mannosamine to mammals. *Nature* 211, 976-977
47. Gagiannis, D., et al. (2007) Engineering the sialic acid in organs of mice using N-propanoylmannosamine. *Biochim Biophys Acta* 1770, 297-306
48. Galeano, B., et al. (2007) Mutation in the key enzyme of sialic acid biosynthesis causes severe glomerular proteinuria and is rescued by N-acetylmannosamine. *J Clinical Investigation* (in press)
49. Rando, T. A. (2004) Artificial sweeteners-enhancing glycosylation to treat muscular dystrophies. *N Engl J Med* 351, 1254-1256
50. Niehues, R., et al. (1998) Carbohydrate-deficient glycoprotein syndrome type Ib. Phosphomannose isomerase deficiency and mannose therapy. *J Clin Invest* 101, 1414-1420
51. de Lonlay, P., et al. (1999) Hyperinsulinemic hypoglycemia as a presenting sign in phosphomannose isomerase deficiency: A new manifestation of carbohydrate-deficient glycoprotein syndrome treatable with mannose. *J Pediatr* 135, 379-383
52. Witt, W., et al. (1979) Uptake and distribution of orally applied N-acetyl-(14C)neuraminosyl-lactose and N-acetyl-(14C)neuraminic acid in the organs of newborn rats. *Nutr Metab* 23, 51-61
53. Hirschberg, C. B., et al. (1976) Sialic acid uptake by fibroblasts. *Biochemistry* 15, 3591-3599
54. Andres, P. L., et al. (1996) A comparison of three measures of disease progression in ALS. *J Neurol Sci* 139 Suppl, 64-70
55. Visser, J., et al. (2003) Comparison of maximal voluntary isometric contraction and hand-held dynamometry in measuring muscle strength of patients with progressive lower motor neuron syndrome. *Neuromuscul Disord* 13, 744-750
56. Brussock, C. M., et al. (1992) Measurement of isometric force in children with and without Duchenne's muscular dystrophy. *Phys Ther* 72, 105-114
57. Andres, P. L., et al. (1986) Quantitative motor assessment in amyotrophic lateral sclerosis. *Neurology* 36, 937-941
58. Jain, M., et al. (2006) Intra-rater and inter-rater reliability of the 10-point Manual Muscle Test (MMT) of strength in children with juvenile idiopathic inflammatory myopathies (JIIM). *Phys Occup Ther Pediatr* 26, 5-17
59. Fix, A. J., and Daughton, D. M. (1998) *Human Activity Profile Professional Manual*. Psychological Assessment Resources Inc
60. Ware, J. E., Jr., and Sherbourne, C. D. (1992) The MOS 36-item short-form health survey (SF-36). I. Conceptual framework and item selection. *Med Care* 30, 473-483
61. Harris-Love, M., et al. (2004) Performance based assessment of functional limitation and muscle endurance: Reliability of the adult myositis assessment tool. *Journal of Neurologic Physical Therapy* Platforms, Thematic Posters, & Posters for CSM 2005.
62. Beck, A. T., et al. (1996) *Manual for the Beck Depression Inventory-II*. Psychological Corporation
63. Belza, B. L. (1995) Comparison of self-reported fatigue in rheumatoid arthritis and controls. *J Rheumatol* 22, 639-643
64. Colombo, R., et al. (2000) Measurement of isometric muscle strength: a reproducibility study of maximal voluntary contraction in normal subjects and amyotrophic lateral sclerosis patients. *Med Eng Phys* 22, 167-174
65. (2003) A comparison of muscle strength testing techniques in amyotrophic lateral sclerosis. *Neurology* 61, 1503-1507
66. Mayhew, J. E., et al. (2007) Reliable surrogate outcome measures in multicenter clinical trials of Duchenne muscular dystrophy. *Muscle Nerve* 35, 36-42
67. Symons, T. B., et al. (2005) Reliability of a single-session isokinetic and isometric strength measurement protocol in older men. *J Gerontol A Biol Sci Med Sci* 60, 114-119

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of treating a condition or disease in a mammal in need thereof comprising selecting a subject with the condition or disease, and administering to the subject an effective amount of N-acetyl mannosamine or a derivative thereof, to the mammal, wherein the derivative consists of Formula I.

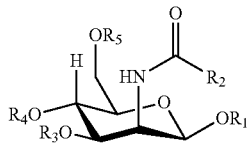

wherein $R_1$, $R_3$, $R_4$, or $R_5$ is hydrogen, lower alkanoyl, carboxylate or lower alkyl; $R_2$ is lower alkyl, lower alkanoylalkyl, lower alkyl alkanoyloxy; and the condition or disease is diabetic nephropathy.

2. The method of claim 1, comprising administering a therapeutic amount of N-acetyl mannosamine to the mammal.

3. The method of claim 2, wherein the therapeutic amount is about 0.1 g to about 50 g N-acetyl mannosamine per day.

4. The method of claim 2, wherein the therapeutic amount is administered in a unit dosage of about 0.01 g to about 50 g N-acetyl mannosamine per unit dosage.

5. The method of claim 1, comprising sustained release of the sialic acid precursor, N-acetyl mannosamine or a derivative thereof.

6. The method of claim 1, comprising topical administration of the sialic acid precursor, N-acetyl mannosamine or a derivative thereof.

7. The method of claims 2, wherein the N-acetyl mannosamine is administered orally to the mammal.

8. The method of claim 2, wherein the N-acetyl mannosamine is microencapsulated.

9. The method of claim 2, wherein the method decreases proteinuria in the mammal.

* * * * *

SEQUENCE LISTING

<160> NUMBER OF SEQ ID NOS: 8

<210> SEQ ID NO 1
<211> LENGTH: 722
<212> TYPE: PRT
<213> ORGANISM: Mus musculus

<400> SEQUENCE: 1

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Ala Phe Phe Glu Leu Asp Val Val Val Leu Gly Ser

```
                35                  40                  45
        His Leu Ile Asp Asp Tyr Gly Asn Thr Tyr Arg Met Ile Glu Gln Asp
         50                  55                  60

Asp Phe Asp Ile Asn Thr Arg Leu His Thr Ile Val Arg Gly Glu Asp
         65                  70                  75                  80

Glu Ala Ala Met Val Glu Ser Val Gly Leu Ala Leu Val Lys Leu Pro
                             85                  90                  95

Asp Val Leu Asn Arg Leu Lys Pro Asp Ile Met Ile Val His Gly Asp
                        100                 105                 110

Arg Phe Asp Ala Leu Ala Leu Ala Thr Ser Ala Ala Leu Met Asn Ile
                    115                 120                 125

Arg Ile Leu His Ile Glu Gly Gly Glu Val Ser Gly Thr Ile Asp Asp
                130                 135                 140

Ser Ile Arg His Ala Ile Thr Lys Leu Ala His Tyr His Val Cys Cys
        145                 150                 155                 160

Thr Arg Ser Ala Glu Gln His Leu Ile Ser Met Cys Glu Asp His Asp
                            165                 170                 175

Arg Ile Leu Leu Ala Gly Cys Pro Ser Tyr Asp Lys Leu Leu Ser Ala
                        180                 185                 190

Lys Asn Lys Asp Tyr Met Ser Ile Ile Arg Met Trp Leu Gly Asp Asp
                    195                 200                 205

Val Lys Cys Lys Asp Tyr Ile Val Ala Leu Gln His Pro Val Thr Thr
                210                 215                 220

Asp Ile Lys His Ser Ile Lys Met Phe Glu Leu Thr Leu Asp Ala Leu
        225                 230                 235                 240

Ile Ser Phe Asn Lys Arg Thr Leu Val Leu Phe Pro Asn Ile Asp Ala
                            245                 250                 255

Gly Ser Lys Glu Met Val Arg Val Met Arg Lys Gly Ile Glu His
                        260                 265                 270

His Pro Asn Phe Arg Ala Val Lys His Val Pro Phe Asp Gln Phe Ile
                    275                 280                 285

Gln Leu Val Ala His Ala Gly Cys Met Ile Gly Asn Ser Ser Cys Gly
                290                 295                 300

Val Arg Glu Val Gly Ala Phe Gly Thr Pro Val Ile Asn Leu Gly Thr
        305                 310                 315                 320

Arg Gln Ile Gly Arg Glu Thr Gly Glu Asn Val Leu His Val Arg Asp
                            325                 330                 335

Ala Asp Thr Gln Asp Lys Ile Leu Gln Ala Leu His Leu Gln Phe Gly
                        340                 345                 350

Lys Gln Tyr Pro Cys Ser Lys Ile Tyr Gly Asp Gly Asn Ala Val Pro
                    355                 360                 365

Arg Ile Leu Lys Phe Leu Lys Ser Ile Asp Leu Gln Glu Pro Leu Gln
                370                 375                 380

Lys Lys Phe Cys Phe Pro Pro Val Lys Glu Asn Ile Ser Gln Asp Ile
        385                 390                 395                 400

Asp His Ile Leu Glu Thr Leu Ser Ala Leu Ala Val Asp Leu Gly Gly
                            405                 410                 415

Thr Asn Leu Arg Val Ala Ile Val Ser Met Lys Gly Glu Ile Val Lys
                        420                 425                 430

Lys Tyr Thr Gln Phe Asn Pro Lys Thr Tyr Glu Glu Arg Ile Ser Leu
                    435                 440                 445

Ile Leu Gln Met Cys Val Glu Ala Ala Ala Glu Ala Val Lys Leu Asn
                450                 455                 460
```

-continued

```
Cys Arg Ile Leu Gly Val Gly Ile Ser Thr Gly Gly Arg Val Asn Pro
465                 470                 475                 480

Gln Glu Gly Val Val Leu His Ser Thr Lys Leu Ile Gln Glu Trp Asn
            485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Met Ala Glu Arg Lys Phe
            515                 520                 525

Gly Gln Gly Lys Gly Gln Glu Asn Phe Val Thr Leu Ile Thr Gly Thr
            530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile His

<210> SEQ ID NO 2
<211> LENGTH: 722
<212> TYPE: PRT
<213> ORGANISM: Artificial Sequence
<220> FEATURE:
<223> OTHER INFORMATION: A synthetic polypeptide

<400> SEQUENCE: 2

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Ala Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95
```

```
Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Cys Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Ser Leu
        435                 440                 445

Ile Leu Gln Met Cys Val Glu Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Gln Glu Gly Val Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Met Ala Glu Arg Lys Phe
```

```
                515                 520                 525
Gly Gln Gly Lys Gly Gln Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
                595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
                675                 680                 685

Ser Ser Val Gln Asp Val Asp Val Val Ser Asp Leu Val Asp Pro
        690                 695                 700

Ala Leu Leu Gly Ala Ala Ser Thr Val Leu Asp Tyr Thr Thr Arg Arg
705                 710                 715                 720

Ile His

<210> SEQ ID NO 3
<211> LENGTH: 2654
<212> TYPE: DNA
<213> ORGANISM: Mus musculus

<400> SEQUENCE: 3
gctaaaccag aggccagacg gcagctcagg agtccgacca cacctcagga aacagctgtg      60
ccacaggatg gaaacacacg cgcatctcca cagggagcag agctacgcag acctcatga     120 actctattt aagaaactct caagtaaaaa gaagcaagtc atggagaaga acgggaacaa     180
ccgaaagctc cgggtttgcg ttgccacctg caaccgagct gactactcca aactggcccc     240
gatcatgttc ggcatcaaga cagagcccgc gttctttgag ttggacgtgg tggtgctcgg     300
ctcccacctg attgacgact atggaaacac ataccgcatg attgagcaag atgactttga     360
cattaacacc aggctccaca cgattgttag aggggaagat gaagcggcca tggtagagtc     420
ggtaggccta gcgctcgtga agctaccgga cgtcctcaat cgcctgaagc ccgacatcat     480
gattgttcac ggagaccgat tgacgcccct tgctctggct acgtctgctg ccttgatgaa     540
catccgcatc cttcacattg aaggaggcga ggtcagcggg accattgatg actctatcag     600
acacgccata acaaaactgg ctcactacca tgtgtgctgc actagaagtg cagagcagca     660
cctgatctct atgtgcgagg accacgaccg catcctgttg gcaggctgcc cttcctatga     720
caaactgctc tccgccaaga caaagactaa tatgagcatc attcggatgt ggctaggcga     780
tgatgtaaaa tgtaaggatt acatcgttgc cctgcagcat cccgtgacca ctgacattaa     840
gcattccata aagatgtttg agctaacact ggatgccctg atctcgttta caagaggac     900 cctagttctg tttccaaata tcgatgcagg cagcaaggag atggttcgag tgatgcggaa     960
```

| | | | | |
|---|---|---|---|---|
| gaagggcatc | gagcatcacc | ccaatttccg | tgcagtcaag | cacgtcccgt ttgaccagtt | 1020 |
| catacagctg | gtcgcccacg | ctggctgcat | gattgggaat | agcagctgcg gcgtgcgaga | 1080 |
| ggttggcgct | ttcggaacac | ccgtgatcaa | cctgggcaca | aggcagatag gaagagaaac | 1140 |
| cggggagaat | gttcttcatg | tcagggatgc | tgacacccaa | gataaaatat tgcaagcact | 1200 |
| acacctccag | ttcggcaaac | agtacccttg | ctcaaagata | tatggggatg gaatgctgt | 1260 |
| tccaaggatt | ttaaagtttc | tcaaatccat | tgaccttcaa | gagccactac agaagaaatt | 1320 |
| ctgcttcccc | cctgtaaagg | agaacatctc | tcaagacatt | gaccacatcc tggaaactct | 1380 |
| gagtgccttg | gctgttgatc | ttggcgggac | aaacctgagg | gtggcaatag ttagcatgaa | 1440 |
| gggtgaaatc | gttaagaagt | acactcagtt | caaccctaaa | acctatgaag aaaggattag | 1500 |
| tttaatcctg | cagatgtgtg | tggaagctgc | cgcggaagct | gtgaaactca attgcagaat | 1560 |
| tctgggagta | ggcatctcca | caggtggccg | cgtgaatccc | caggaaggag ttgtgctgca | 1620 |
| ttcaaccaag | ctgatccagg | aatggaactc | cgtggacctc | aggacacccc tctccgacac | 1680 |
| cctgcatctc | cccgtgtggg | tggacaatga | cggcaactgt | gccgccatgg cagagaggaa | 1740 |
| gttcggccaa | ggaaaaggac | aggagaactt | cgtgacgctc | atcacgggga cagggatcgg | 1800 |
| tggggggatc | atccaccagc | acgaactgat | ccacggcagc | tccttctgcg cggcggagct | 1860 |
| cggccatctc | gtggtgtccc | tggacggtcc | tgactgctcc | tgtggaagcc atgggtgcat | 1920 |
| cgaagcgtac | gcctctggaa | tggccttgca | gagggaagca | agaaactcc atgatgagga | 1980 |
| cctgctcttg | gtggaaggga | tgtcagtacc | aaaagacgaa | gctgtgggtg ccctccatct | 2040 |
| catccaggct | gccaagctgg | gcaacgtgaa | ggcccagagc | atcttacgaa cagctggaac | 2100 |
| tgctttggga | cttggggttg | tgaacatcct | ccacactatg | aatccttccc tggtgatcct | 2160 |
| gtctggagtc | ctggccagtc | actacatcca | catcgtgaag | gacgtcatcc gccagcaagc | 2220 |
| cttgtcctcc | gtgcaggatg | tggacgtggt | ggtctcagac | ttggtggacc cggccctgct | 2280 |
| tggcgcagcc | agcatggttc | tggactacac | aacgcgcagg | atccactagg tctcccggga | 2340 |
| acggacacgg | acagagactc | gggagctgct | tagagtggaa | ccatgctctt ctagatcagt | 2400 |
| gtttctgcga | aggcaaattt | gggggagggg | ctgctgagac | agctcagtgg ttaagagcct | 2460 |
| gccctgctcc | tgccagtccc | cagcacccat | gtcaggcagc | tcagctgcct ggaagccaag | 2520 |
| ctccagggga | cccaatgcct | ctctgccggg | ggcagctgca | ctcagatgta catacccctc | 2580 |
| tccacacaca | tacaaataaa | gcttattttt | caaaaggcaa | aaaaaaaaa aaaaaaaaa | 2640 |
| aaaaaaaaaa | aaaa | | | | 2654 |

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 4
agcacttcct gagtttgatg        20

<210> SEQ ID NO 5
<211> LENGTH: 22
<212> TYPE: DNA
<213> ORGANISM: Artificial Sequence
<220> FEATURE:
<223> OTHER INFORMATION: A synthetic oligonucleotide

```
<400> SEQUENCE: 5
atttgccttc gcagacactt ga                                          22

<210> SEQ ID NO 6
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 6
gcccagagca tcttacgaac                                             20

<210> SEQ ID NO 7
<211> LENGTH: 18
<212> TYPE: PRT
<213> ORGANISM: Artificial Sequence
<220> FEATURE:
<223> OTHER INFORMATION: A synthetic oligonucleotide

<400> SEQUENCE: 7

Gly Gly Gly Thr Cys Cys Cys Cys Thr Gly Gly Ala Gly Cys Thr Thr
1               5                   10                  15

Gly Gly

<210> SEQ ID NO 8
<211> LENGTH: 20
<212> TYPE: PRT
<213> ORGANISM: Mus musculus

<400> SEQUENCE: 8

Glu Ala Tyr Ala Ser Gly Met Ala Leu Gln Arg Glu Ala Lys Lys Leu
1               5                   10                  15

His Asp Glu Asp
            20
```